United States Patent
Ludwig et al.

(10) Patent No.: US 10,441,430 B2
(45) Date of Patent: Oct. 15, 2019

(54) EXPANDABLE SPINAL IMPLANTS

(71) Applicant: K2M, Inc., Leesburg, VA (US)

(72) Inventors: Steven Ludwig, Baltimore, MD (US); Scott Dhupar, Windsor, CO (US); Sabatino Bianco, Arlington, TX (US); Khalid Abbed, New Haven, CT (US); Egon Doppenberg, Lake Bluff, IL (US); Jennifer Moore, Leesburg, VA (US); John Donohoe, Morrisville, NC (US); Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 141 days.

(21) Appl. No.: 15/657,796

(22) Filed: Jul. 24, 2017

(65) Prior Publication Data
US 2019/0021868 A1 Jan. 24, 2019

(51) Int. Cl.
*A61F 2/44* (2006.01)
*A61F 2/46* (2006.01)

(52) U.S. Cl.
CPC ............ *A61F 2/442* (2013.01); *A61F 2/4611* (2013.01); *A61F 2002/443* (2013.01)

(58) Field of Classification Search
CPC ... A61F 2/442; A61F 2/4611; A61F 2002/443
See application file for complete search history.

(56) References Cited

U.S. PATENT DOCUMENTS

| | | |
|---|---|---|
| 4,401,112 A | 8/1983 | Rezaian |
| 4,657,550 A | 4/1987 | Daher |
| 5,171,278 A | 12/1992 | Pisharodi |
| 5,236,460 A | 8/1993 | Barber |
| 5,290,312 A | 3/1994 | Kojimoto et al. |
| 5,397,364 A | 3/1995 | Kozak et al. |
| 5,554,191 A | 9/1996 | Lahille et al. |
| 5,571,192 A | 11/1996 | Schonhoffer |
| 5,653,762 A | 8/1997 | Pisharodi |
| 5,653,763 A | 8/1997 | Errico et al. |
| 5,665,122 A | 9/1997 | Kambin |

(Continued)

FOREIGN PATENT DOCUMENTS

| | | |
|---|---|---|
| SU | 1560184 A1 | 4/1990 |
| WO | 9848739 A1 | 11/1998 |

(Continued)

*Primary Examiner* — Christian A Sevilla
(74) *Attorney, Agent, or Firm* — Lerner, David, Littenberg, Krumholz & Mentlik, LLP

(57) ABSTRACT

A spinal implant has proximal and distal regions, and includes upper and lower bodies. A proximal adjustment assembly is disposed between the upper and lower bodies in the proximal region of the spinal implant and is adjustably coupled to the upper and lower bodies, and a distal adjustment assembly is disposed between the upper and lower bodies in the distal region of the spinal implant and is adjustably coupled to the upper and lower bodies. The proximal and distal adjustment assemblies are independently movable with respect to each other, both concurrently and alternately, to change a vertical height of at least one of the proximal or distal regions of the spinal implant. A set screw is removably disposed within the proximal region of the spinal implant to lock the vertical height of the proximal and distal regions of the spinal implant.

27 Claims, 35 Drawing Sheets

(56) References Cited

U.S. PATENT DOCUMENTS

| | | |
|---|---|---|
| 5,702,455 A | 12/1997 | Saggar |
| 5,865,848 A | 2/1999 | Baker |
| 5,916,267 A | 6/1999 | Tienboon |
| 5,989,290 A | 11/1999 | Biedermann et al. |
| 6,015,436 A | 1/2000 | Schonhoffer |
| 6,045,579 A | 4/2000 | Hochshuler et al. |
| 6,102,950 A | 8/2000 | Vaccaro |
| 6,159,244 A | 12/2000 | Suddaby |
| 6,174,334 B1 | 1/2001 | Suddaby |
| 6,176,881 B1 | 1/2001 | Schar et al. |
| 6,176,882 B1 | 1/2001 | Biedermann et al. |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,214,050 B1 | 4/2001 | Huene |
| 6,296,665 B1 | 10/2001 | Strnad et al. |
| 6,332,895 B1 | 12/2001 | Suddaby |
| 6,344,057 B1 | 2/2002 | Rabbe et al. |
| 6,352,556 B1 | 3/2002 | Kretschmer et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,031 B1 | 5/2002 | Foley et al. |
| 6,395,034 B1 | 5/2002 | Suddaby |
| 6,409,766 B1 | 6/2002 | Brett |
| 6,419,705 B1 | 7/2002 | Erickson |
| 6,436,140 B1 | 8/2002 | Liu et al. |
| 6,436,142 B1 | 8/2002 | Paes et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,491,724 B1 | 12/2002 | Ferree |
| 6,524,341 B2 | 2/2003 | Lang et al. |
| 6,562,074 B2 | 5/2003 | Gerbec et al. |
| 6,576,016 B1 | 6/2003 | Hochshuler et al. |
| 6,610,090 B1 | 8/2003 | Bohm et al. |
| 6,616,695 B1 | 9/2003 | Crozet et al. |
| 6,641,614 B1 | 11/2003 | Wagner et al. |
| 6,685,742 B1 | 2/2004 | Jackson |
| 6,716,247 B2 | 4/2004 | Michelson |
| 6,773,460 B2 | 8/2004 | Jackson |
| 6,783,547 B2 | 8/2004 | Castro |
| 6,808,537 B2 | 10/2004 | Michelson |
| 6,814,756 B1 | 11/2004 | Michelson |
| 6,821,298 B1 | 11/2004 | Jackson |
| 6,866,682 B1 | 3/2005 | An et al. |
| 6,902,579 B2 | 6/2005 | Harms et al. |
| 6,955,691 B2 | 10/2005 | Chae et al. |
| 6,962,606 B2 | 11/2005 | Michelson |
| 6,972,035 B2 | 12/2005 | Michelson |
| 7,008,453 B1 | 3/2006 | Michelson |
| 7,018,415 B1 | 3/2006 | McKay |
| 7,022,138 B2 | 4/2006 | Mashburn |
| 7,029,498 B2 | 4/2006 | Boehm et al. |
| 7,044,971 B2 | 5/2006 | Suddaby |
| 7,056,343 B2 | 6/2006 | Schafer et al. |
| 7,087,055 B2 | 8/2006 | Lim et al. |
| 7,094,257 B2 | 8/2006 | Mujwid et al. |
| 7,118,579 B2 | 10/2006 | Michelson |
| 7,156,874 B2 | 1/2007 | Paponneau et al. |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,311,733 B2 | 12/2007 | Metz-Stavenhagen |
| 7,431,735 B2 | 10/2008 | Liu et al. |
| 7,458,988 B2 | 12/2008 | Trieu et al. |
| 7,544,208 B1 | 6/2009 | Mueller et al. |
| 7,547,325 B2 | 6/2009 | Biedermann et al. |
| 7,575,601 B2 | 8/2009 | Dickson |
| 7,588,573 B2 | 9/2009 | Berry |
| 7,615,078 B2 | 11/2009 | White et al. |
| 7,618,458 B2 | 11/2009 | Biedermann et al. |
| 7,621,953 B2 | 11/2009 | Braddock, Jr. et al. |
| 7,641,693 B2 | 1/2010 | Gutlin et al. |
| 7,655,027 B2 | 2/2010 | Michelson |
| 7,674,296 B2 | 3/2010 | Rhoda et al. |
| 7,678,148 B2 | 3/2010 | Peterman |
| 7,691,147 B2 | 4/2010 | Gutlin et al. |
| 7,708,779 B2 | 5/2010 | Edie |
| 7,731,752 B2 | 6/2010 | Edie et al. |
| 7,744,650 B2 | 6/2010 | Lindner et al. |
| 7,758,648 B2 | 7/2010 | Castleman et al. |
| 7,763,028 B2 | 7/2010 | Lim et al. |
| 7,794,501 B2 | 9/2010 | Edie et al. |
| 7,799,081 B2 | 9/2010 | McKinley |
| 7,803,191 B2 | 9/2010 | Biedermann et al. |
| 7,815,683 B2 | 10/2010 | Melkent et al. |
| 7,819,920 B2 | 10/2010 | Assaker |
| 7,819,921 B2 | 10/2010 | Grotz |
| 7,819,922 B2 | 10/2010 | Sweeney |
| 7,828,849 B2 | 11/2010 | Lim |
| 7,850,733 B2 | 12/2010 | Baynham et al. |
| 7,862,618 B2 | 1/2011 | White et al. |
| 7,875,078 B2 | 1/2011 | Wysocki et al. |
| 7,879,098 B1 | 2/2011 | Simmons, Jr. |
| 7,883,542 B2 | 2/2011 | Zipnick |
| 7,887,596 B2 | 2/2011 | Douget et al. |
| 7,909,870 B2 | 3/2011 | Kraus |
| 7,914,581 B2 | 3/2011 | Dickson et al. |
| 7,959,677 B2 | 6/2011 | Landry et al. |
| 7,967,867 B2 | 6/2011 | Barreiro et al. |
| 7,981,158 B2 | 7/2011 | Fitz et al. |
| 8,034,111 B2 | 10/2011 | Hsu et al. |
| 8,062,366 B2 | 11/2011 | Melkent |
| 8,062,368 B2 | 11/2011 | Heinz et al. |
| 8,062,375 B2 | 11/2011 | Glerum et al. |
| 8,070,817 B2 | 12/2011 | Gradl et al. |
| 8,105,382 B2 | 1/2012 | Olmos et al. |
| 8,110,004 B2 | 2/2012 | Valdevit et al. |
| 8,118,871 B2 | 2/2012 | Gordon et al. |
| 8,123,809 B2 | 2/2012 | Melkent et al. |
| 8,128,701 B2 | 3/2012 | Kast |
| 8,133,232 B2 | 3/2012 | Levy et al. |
| 8,152,852 B2 | 4/2012 | Biyani |
| 8,157,864 B2 | 4/2012 | Rogeau et al. |
| 8,163,020 B2 | 4/2012 | Le Huec |
| 8,177,846 B2 | 5/2012 | Blackwell et al. |
| 8,182,535 B2 | 5/2012 | Kraus |
| 8,182,537 B2 | 5/2012 | Refai et al. |
| 8,187,328 B2 | 5/2012 | Melkent |
| 8,187,331 B2 | 5/2012 | Strohkirch, Jr. et al. |
| 8,197,546 B2 | 6/2012 | Doubler et al. |
| 8,202,321 B2 | 6/2012 | Gerner |
| 8,211,178 B2 | 7/2012 | Melkent et al. |
| 8,221,502 B2 | 7/2012 | Branch, Jr. |
| 8,241,294 B2 | 8/2012 | Sommerich et al. |
| 8,241,358 B2 | 8/2012 | Butler et al. |
| 8,241,363 B2 | 8/2012 | Sommerich et al. |
| 8,252,054 B2 | 8/2012 | Greenhalgh et al. |
| 8,267,939 B2 | 9/2012 | Cipoletti et al. |
| 8,268,002 B2 | 9/2012 | Blackwell et al. |
| 8,268,004 B2 | 9/2012 | Castleman et al. |
| 8,273,124 B2 | 9/2012 | Renganath et al. |
| 8,273,126 B2 | 9/2012 | Lindner |
| 8,292,963 B2 | 10/2012 | Miller et al. |
| 8,308,802 B2 | 11/2012 | Rhoda et al. |
| 8,317,866 B2 | 11/2012 | Palmatier et al. |
| 8,328,871 B2 | 12/2012 | Capote et al. |
| 8,337,558 B2 | 12/2012 | Lindner |
| 8,353,963 B2 | 1/2013 | Glerum |
| 8,366,777 B2 | 2/2013 | Matthis et al. |
| 8,377,140 B2 | 2/2013 | DeFalco et al. |
| 8,382,842 B2 | 2/2013 | Greenhalgh et al. |
| 8,398,713 B2 | 3/2013 | Weiman |
| 8,409,283 B2 | 4/2013 | Drochner et al. |
| 8,409,291 B2 | 4/2013 | Blackwell et al. |
| 8,425,608 B2 | 4/2013 | Dewey et al. |
| 8,435,298 B2 | 5/2013 | Weiman |
| 8,452,611 B1 | 5/2013 | Johnson et al. |
| 8,486,147 B2 | 7/2013 | de Villiers et al. |
| 8,496,706 B2 | 7/2013 | Ragab et al. |

(56) References Cited

U.S. PATENT DOCUMENTS

| | | |
|---|---|---|
| 8,506,635 B2 | 8/2013 | Palmatier et al. |
| 8,518,114 B2 | 8/2013 | Marik |
| 8,518,120 B2 | 8/2013 | Glerum et al. |
| 8,535,380 B2 | 9/2013 | Greenhalgh et al. |
| 8,540,770 B2 | 9/2013 | Woodburn, Sr. et al. |
| 8,551,173 B2 | 10/2013 | Lechmann et al. |
| 8,574,300 B2 | 11/2013 | McManus et al. |
| 8,585,763 B2 | 11/2013 | Olevsky et al. |
| 8,591,585 B2 | 11/2013 | McLaughlin et al. |
| 8,628,576 B2 | 1/2014 | Triplett et al. |
| 8,628,578 B2 | 1/2014 | Miller et al. |
| 8,657,882 B2 | 2/2014 | Bonin, Jr. |
| 8,663,329 B2 | 3/2014 | Ernst |
| 8,679,183 B2 | 3/2014 | Glerum et al. |
| 8,685,095 B2 | 4/2014 | Miller et al. |
| 8,740,980 B2 | 6/2014 | Merves |
| 8,795,366 B2 | 8/2014 | Varela |
| 8,845,733 B2 | 9/2014 | O'Neil et al. |
| 8,876,905 B2 | 11/2014 | Frasier |
| 8,894,712 B2 | 11/2014 | Varela |
| 8,992,620 B2 | 3/2015 | Ashley et al. |
| 9,028,550 B2 | 5/2015 | Shulock et al. |
| 9,492,288 B2 | 11/2016 | Wagner et al. |
| 9,622,878 B2 | 4/2017 | Grotz |
| 2001/0039456 A1 | 11/2001 | Boyer et al. |
| 2002/0068976 A1 | 6/2002 | Jackson |
| 2004/0087947 A1 | 5/2004 | Lim et al. |
| 2004/0186569 A1 | 9/2004 | Berry |
| 2004/0210312 A1 | 10/2004 | Neumann |
| 2004/0215191 A1 | 10/2004 | Kitchen |
| 2004/0254643 A1 | 12/2004 | Jackson |
| 2005/0015149 A1 | 1/2005 | Michelson |
| 2005/0060036 A1 | 3/2005 | Schultz et al. |
| 2005/0125061 A1 | 6/2005 | Zucherman et al. |
| 2005/0283245 A1 | 12/2005 | Gordon et al. |
| 2006/0058879 A1 | 3/2006 | Metz-Stavenhagen |
| 2006/0122701 A1 | 6/2006 | Kiester |
| 2006/0167547 A1 | 7/2006 | Suddaby |
| 2007/0123987 A1 | 5/2007 | Bernstein |
| 2007/0270964 A1 | 11/2007 | Strohkirch et al. |
| 2008/0021559 A1 | 1/2008 | Thramann |
| 2008/0058931 A1 | 3/2008 | White et al. |
| 2008/0114467 A1 | 5/2008 | Capote et al. |
| 2008/0161933 A1 | 7/2008 | Grotz et al. |
| 2008/0167720 A1 | 7/2008 | Melkent |
| 2008/0177387 A1 | 7/2008 | Parimore et al. |
| 2008/0243254 A1 | 10/2008 | Butler |
| 2008/0281424 A1 | 11/2008 | Parry et al. |
| 2008/0288071 A1 | 11/2008 | Biyani et al. |
| 2009/0112325 A1 | 4/2009 | Refai et al. |
| 2009/0216331 A1 | 8/2009 | Grotz et al. |
| 2009/0281625 A1 | 11/2009 | Enayati |
| 2009/0292361 A1 | 11/2009 | Lopez |
| 2010/0016969 A1 | 1/2010 | Richter et al. |
| 2010/0082106 A1 | 4/2010 | Muhanna |
| 2010/0082109 A1 | 4/2010 | Greenhalgh et al. |
| 2010/0094424 A1 | 4/2010 | Woodburn et al. |
| 2010/0145455 A1 | 6/2010 | Simpson et al. |
| 2010/0191336 A1 | 7/2010 | Greenhalgh |
| 2010/0211176 A1 | 8/2010 | Greenhalgh |
| 2010/0249846 A1 | 9/2010 | Simonson |
| 2011/0015741 A1 | 1/2011 | Melkent et al. |
| 2011/0035009 A1 | 2/2011 | Sweeney |
| 2011/0035011 A1* | 2/2011 | Cain ............... A61F 2/442 623/17.16 |
| 2011/0138948 A1 | 6/2011 | Jimenez et al. |
| 2011/0172774 A1 | 7/2011 | Varela |
| 2011/0184524 A1 | 7/2011 | Wiedenbeck et al. |
| 2011/0190890 A1 | 8/2011 | Blackwell et al. |
| 2011/0251692 A1 | 10/2011 | McLaughlin et al. |
| 2011/0264220 A1 | 10/2011 | Miller |
| 2011/0282453 A1* | 11/2011 | Greenhalgh ....... A61B 17/8858 623/17.16 |
| 2011/0319997 A1 | 12/2011 | Glerum et al. |
| 2012/0016476 A1 | 1/2012 | Wilfong et al. |
| 2012/0016478 A1 | 1/2012 | Wilfong et al. |
| 2012/0019307 A1 | 1/2012 | Ludwig |
| 2012/0029635 A1 | 2/2012 | Schoenhoeffer et al. |
| 2012/0029638 A1 | 2/2012 | Miller et al. |
| 2012/0029640 A1 | 2/2012 | Capote et al. |
| 2012/0071977 A1 | 3/2012 | Oglaza et al. |
| 2012/0109302 A1 | 5/2012 | Miller et al. |
| 2012/0143341 A1* | 6/2012 | Zipnick ............ A61B 17/32001 623/17.16 |
| 2012/0197398 A1 | 8/2012 | Miller et al. |
| 2012/0209384 A1 | 8/2012 | Arnold et al. |
| 2012/0226356 A1 | 9/2012 | Hirschl |
| 2012/0232660 A1 | 9/2012 | Davenport |
| 2012/0310350 A1 | 12/2012 | Farris et al. |
| 2012/0323329 A1 | 12/2012 | Jimenez et al. |
| 2012/0330421 A1 | 12/2012 | Weiman |
| 2013/0103156 A1 | 4/2013 | Packer et al. |
| 2013/0110248 A1* | 5/2013 | Zipnick ............... A61F 2/4455 623/17.16 |
| 2013/0116791 A1 | 5/2013 | Theofilos |
| 2013/0158663 A1 | 6/2013 | Miller et al. |
| 2013/0158664 A1 | 6/2013 | Palmatier et al. |
| 2013/0197642 A1 | 8/2013 | Ernst |
| 2013/0197648 A1 | 8/2013 | Boehm et al. |
| 2013/0211526 A1 | 8/2013 | Alheidt et al. |
| 2014/0067069 A1 | 3/2014 | Lopez |
| 2014/0088714 A1 | 3/2014 | Miller et al. |
| 2014/0142706 A1 | 5/2014 | Hansell et al. |
| 2014/0180419 A1 | 6/2014 | Dmuschewsky |
| 2014/0236296 A1* | 8/2014 | Wagner ............. A61F 2/447 623/17.15 |
| 2014/0236297 A1* | 8/2014 | Iott ................. A61F 2/447 623/17.15 |
| 2014/0277501 A1 | 9/2014 | Northcutt et al. |
| 2015/0057753 A1 | 2/2015 | Barrus et al. |
| 2015/0057755 A1 | 2/2015 | Suddaby et al. |
| 2016/0058575 A1 | 3/2016 | Sutterlin, III et al. |
| 2017/0135824 A1 | 5/2017 | Suddaby et al. |

FOREIGN PATENT DOCUMENTS

| | | |
|---|---|---|
| WO | 2013158294 A1 | 10/2013 |
| WO | 2013181024 A1 | 12/2013 |

\* cited by examiner

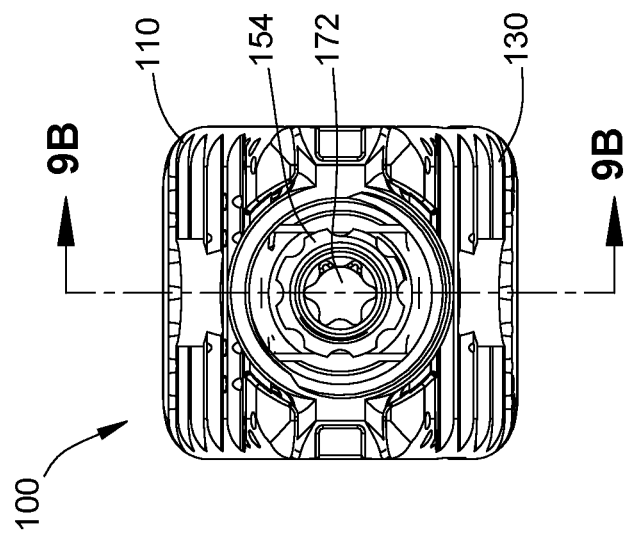
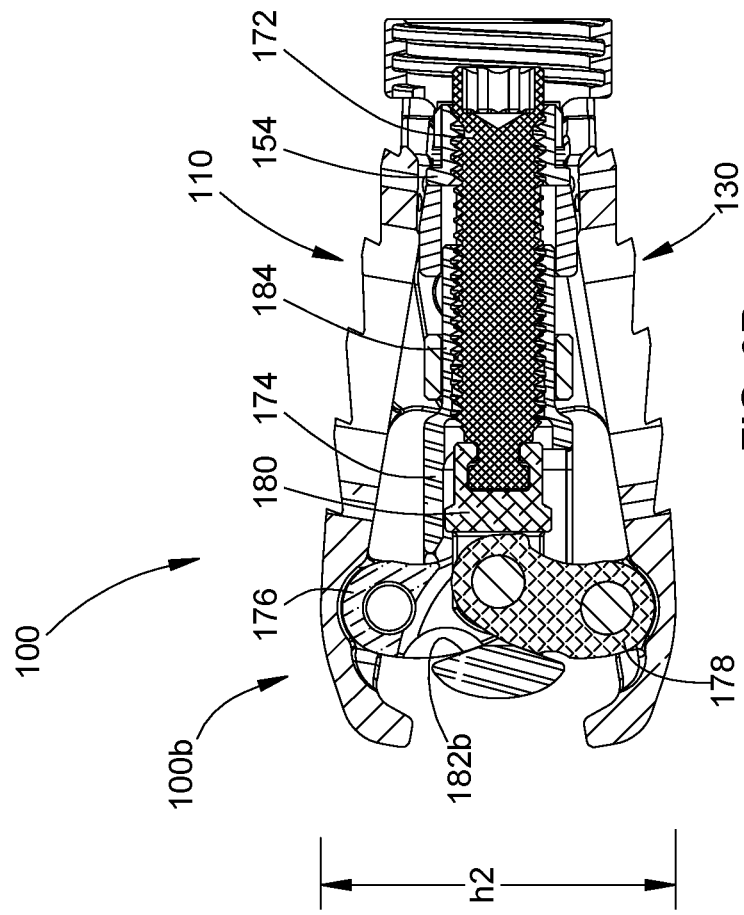

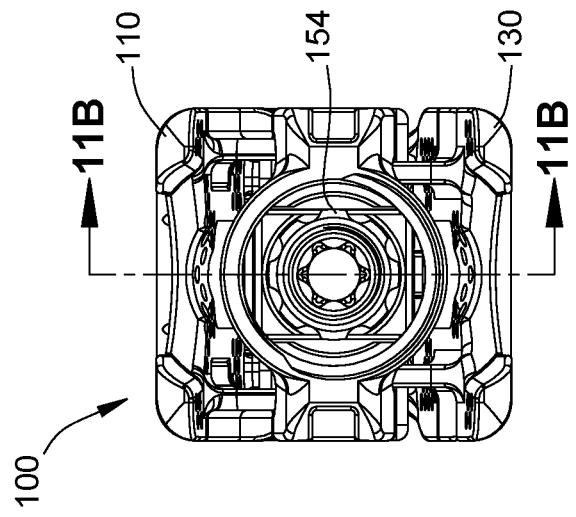
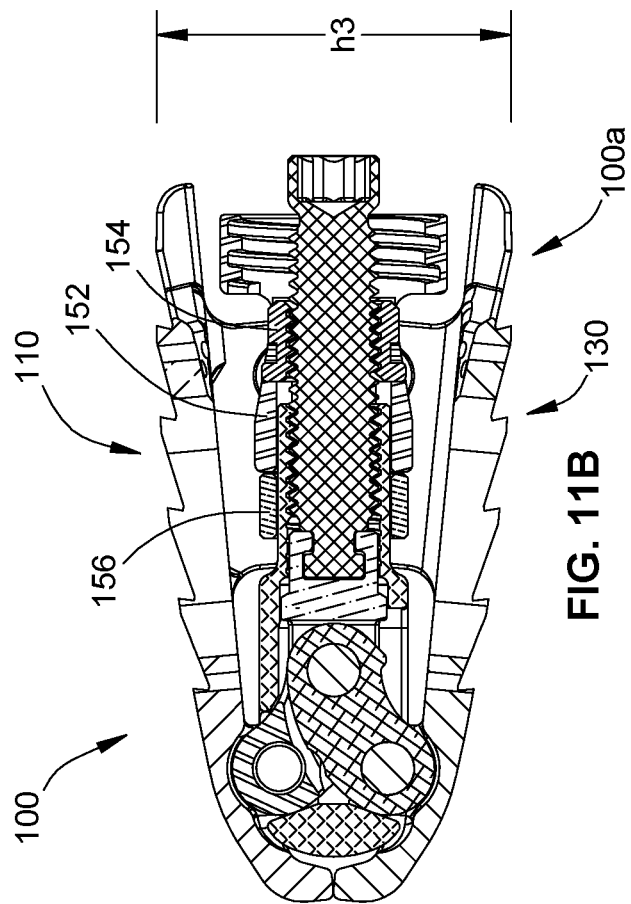

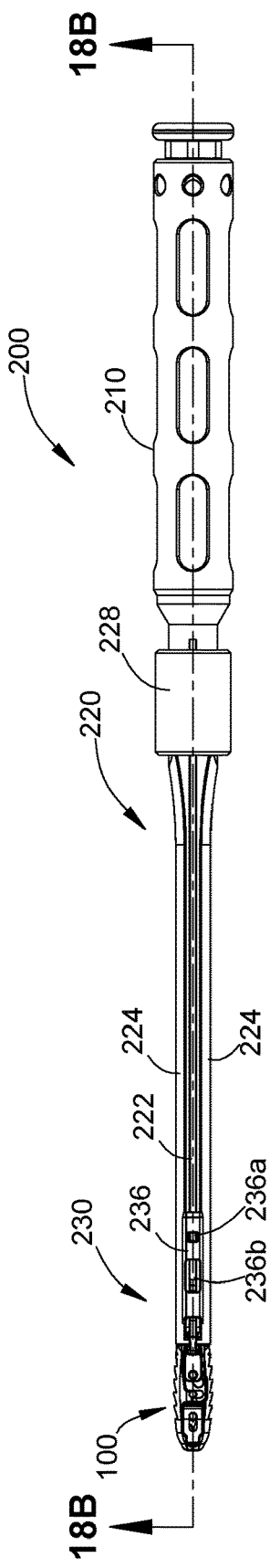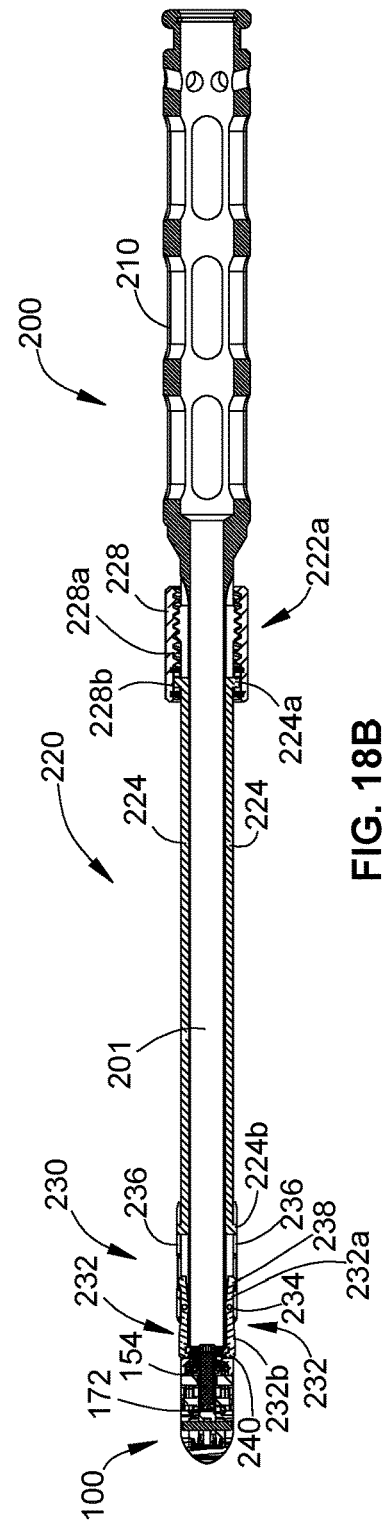
FIG. 18A
FIG. 18B

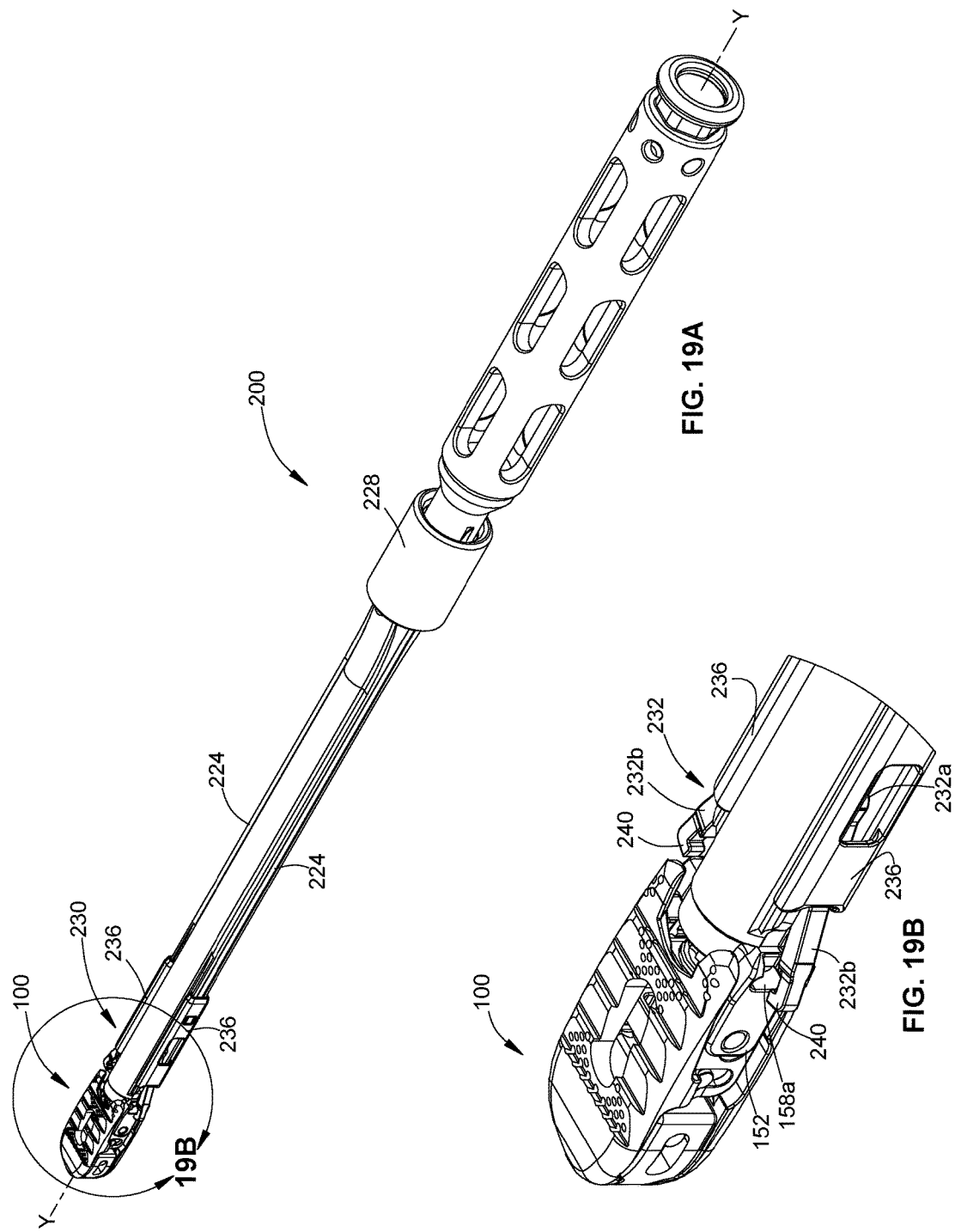

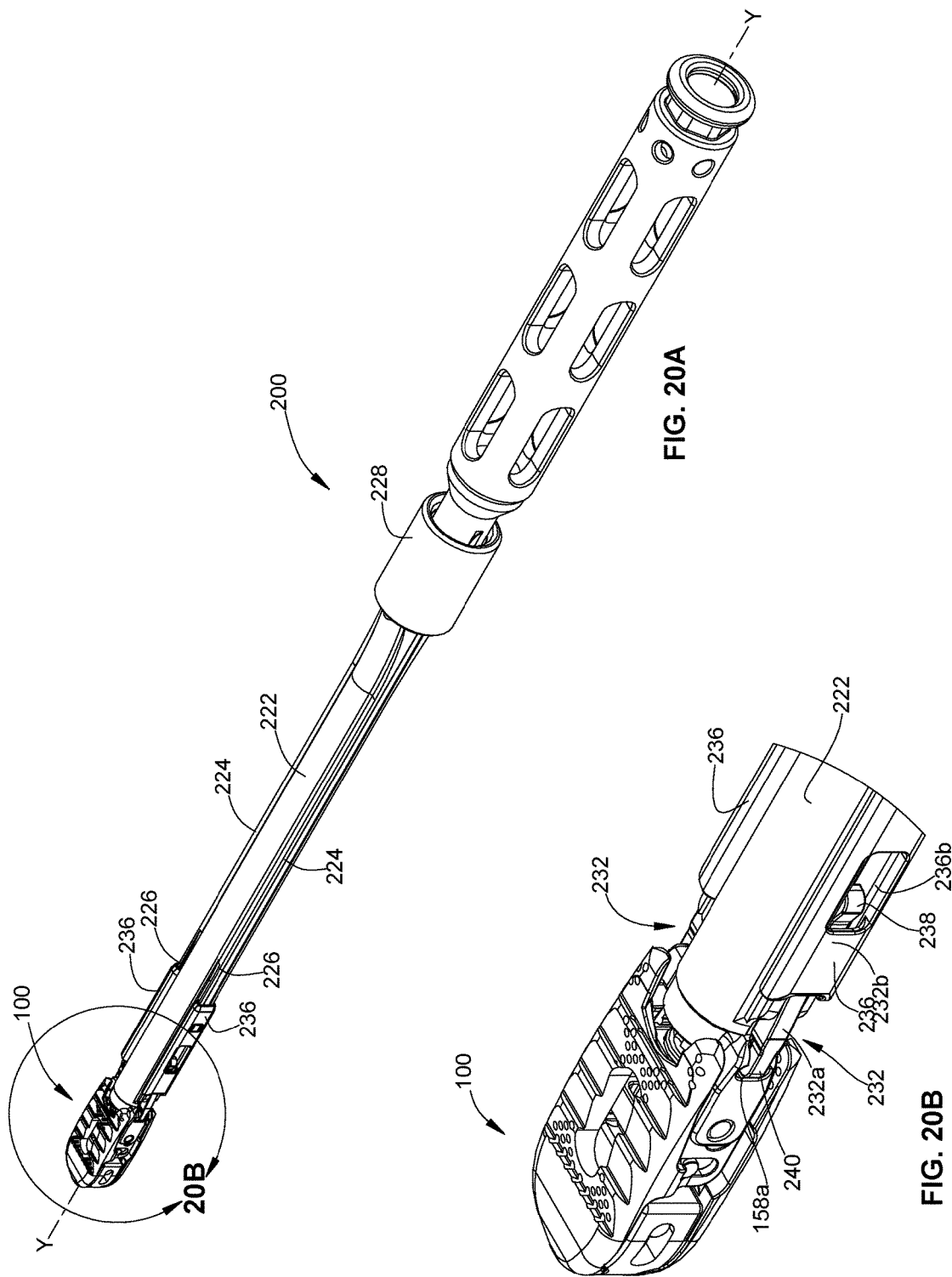

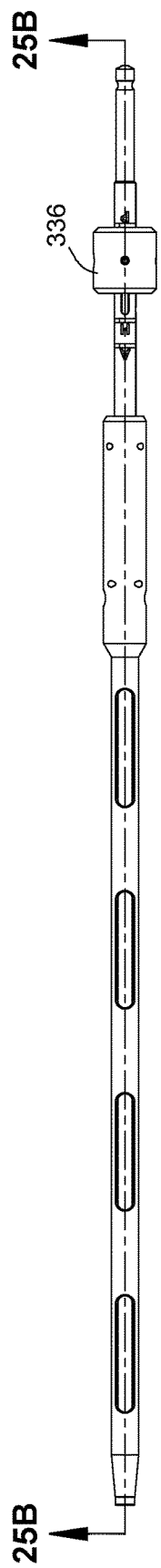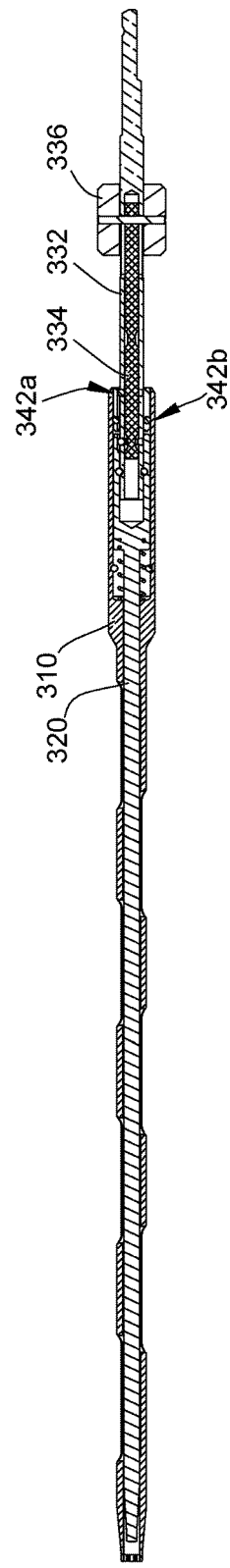
FIG. 25A
FIG. 25B

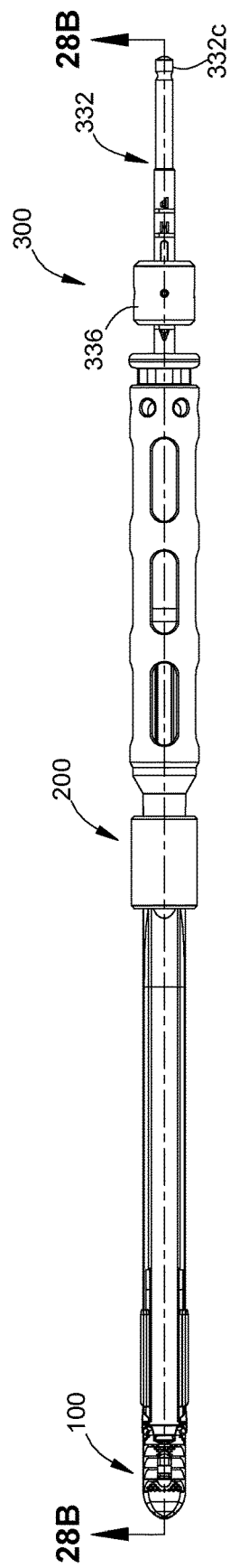
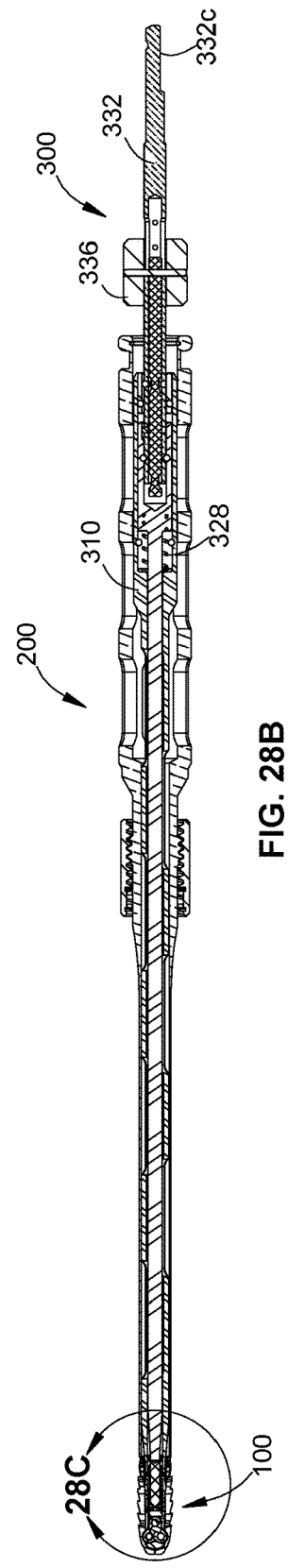
FIG. 28A
FIG. 28B

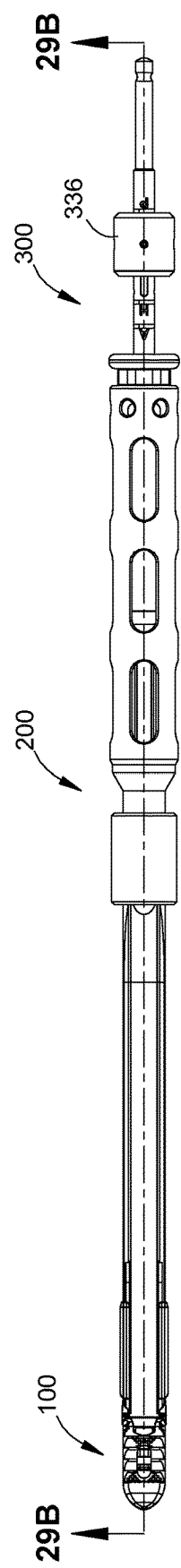
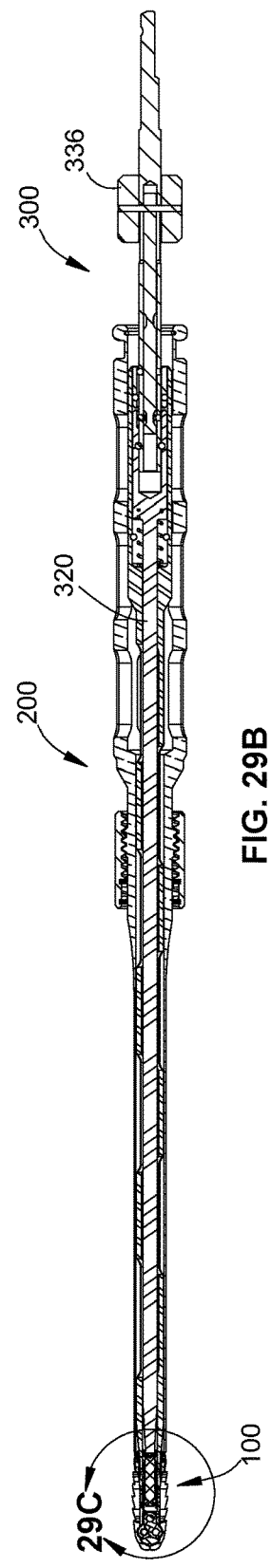
FIG. 29A
FIG. 29B

EXPANDABLE SPINAL IMPLANTS

TECHNICAL FIELD

The present disclosure relates generally to orthopedic surgical devices, and more particularly, to expandable spinal implants configured for positioning within an intervertebral space, associated instrumentation, and methods of using the same.

BACKGROUND

The spinal column is a complex system of bones and connective tissues that provide support for the human body and protection for the spinal cord and nerves. The adult spine includes an upper portion and a lower portion. The upper portion contains twenty-four discrete bones, which are subdivided into three areas including seven cervical vertebrae, twelve thoracic vertebrae, and five lumbar vertebrae. The lower portion includes the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

Spinal discs between the endplates of adjacent vertebrae in a spinal column of the human body provide critical support. However, due to injury, degradation, disease, or the like, these discs can rupture, degenerate, and/or protrude to such a degree that the intervertebral space between adjacent vertebrae collapses as the disc loses at least a part of its support function. This can cause impingement of the nerve roots and severe pain.

In some cases, surgical correction may be required. Some surgical corrections include the removal of the natural spinal disc from between the adjacent vertebrae. In order to preserve the intervertebral disc space for proper spinal column function, an interbody spacer can be inserted between the adjacent vertebrae.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth or fusion has occurred. Due to the concave nature of the vertebral body endplates, it can be challenging to obtain enough contact between the implant and the endplates to create bone growth. Additionally, achieving the desired lordosis can be difficult given the limitation of typical prosthetic implants once they are implanted.

Therefore, a need exists for a spinal implant that provides maximum contact with the vertebral body endplates, matches the desired amount of lordosis, allows for bone growth between adjacent vertebrae, maintains the space between adjacent vertebrae during bone ingrowth, and/or resists dislocation from its implantation site.

SUMMARY

In accordance with an aspect of the present disclosure, a spinal implant having a proximal region and a distal region includes an upper body, a lower body, a proximal adjustment assembly, a distal adjustment assembly, and a set screw. Each of the upper and lower bodies includes an outer surface and an inner surface, and the inner surfaces of the upper and lower bodies are disposed in opposed relation relative to each other. The proximal adjustment assembly is disposed between the upper and lower bodies in the proximal region of the spinal implant and is adjustably coupled to the upper and lower bodies. The distal adjustment assembly is disposed between the upper and lower bodies in the distal region of the spinal implant and is adjustably coupled to the upper and lower bodies. The proximal and distal adjustment assemblies are independently movable, both concurrently and alternately, to change a vertical height of at least one of the proximal region or the distal region of the spinal implant. The set screw is removably disposed within the proximal region of the spinal implant to lock the vertical height of the proximal and distal regions of the spinal implant.

In embodiments, the distal adjustment assembly includes a pivot linkage assembly including an upper pivot linkage pivotably connected to the inner surface of the upper body, a lower pivot linkage pivotably connected to the inner surface of the lower body, and a connector linkage pivotably connected to the upper and lower pivot linkages. Longitudinal movement of the connector linkage causes a corresponding movement of the upper and lower pivot linkages with respect to each other to change the vertical height of the distal region of the spinal implant. In some embodiments, the distal adjustment assembly includes a threaded post including an elongated threaded body extending through the proximal adjustment assembly and a distal end disposed within a recess defined in the connector linkage such that longitudinal translation of the threaded post effects movement of the pivot linkage assembly.

The distal adjustment assembly may include an expander including a body portion defining a cavity therein and a distal end including a double ramped inner surface. The pivot linkage assembly may extend through the cavity of the expander such that the upper and lower pivot linkages contact the double ramped inner surface of the expander when moved by the threaded post. The expander may include a shaft extending proximally from the body portion. The shaft may include a threaded opening defined therein and the elongated threaded body of the threaded post may be threadably engaged with the threaded opening of the shaft and axially movable therethrough into the cavity of the expander.

In embodiments, each of the inner surfaces of the upper and lower bodies includes a pair of proximal fins defining angled slots therethrough, and the proximal adjustment assembly includes a linkage body including distal holes defined through lateral sides thereof and a first set of pins disposed within the distal holes of the linkage body and into the angled slots of the upper and lower bodies. Movement of the linkage body causes the first set of pins to translate within the angled slots to change the vertical height of the proximal region of the spinal implant.

In some embodiments, the proximal adjustment assembly includes a flange nut having a threaded opening defined therethrough that is threadably engaged with the threaded post of the distal adjustment assembly, and the linkage body includes a recess disposed between proximal and distal portions thereof in which the flange nut is disposed. Axial movement of the flange nut along the threaded post effects movement of the linkage body. In certain embodiments, the proximal portion of the linkage body includes a threaded inner surface and the set screw includes a threaded outer surface threadably engageable with the threaded inner surface of the linkage body to prevent the threaded post and the flange nut from moving proximally with respect to the linkage body.

The pair of proximal fins of the upper and lower bodies may define vertical slots therethrough, and the proximal adjustment assembly may include a coupler that includes a pair of nubs extending from lateral sides thereof that is slidably disposed within the vertical slots of the upper and lower bodies.

At least one of the outer surfaces of the upper body or the lower body may include a plurality of tapered ridges.

In accordance with another aspect of the present disclosure, a system includes a spinal implant and an insertion instrument. The spinal implant has a proximal region and a distal region, and includes an upper body, a lower body, a proximal adjustment assembly, and a distal adjustment assembly. Each of the upper and lower bodies includes an outer surface and an inner surface, and the inner surfaces of the upper and lower bodies are disposed in opposed relation relative to each other. The proximal adjustment assembly is disposed between the upper and lower bodies in the proximal region of the spinal implant and is adjustably coupled to the upper and lower bodies. The distal adjustment assembly is disposed between the upper and lower bodies in the distal region of the spinal implant and is adjustably coupled to the upper and lower bodies. The proximal and distal adjustment assemblies are independently movable, both concurrently and alternately, to change a vertical height of at least one of the proximal region or the distal region of the spinal implant. The insertion instrument includes a body portion having an elongated shaft extending along a longitudinal axis, and a connector assembly including connector arms pivotably secured to opposed sides of the elongated shaft. The connector arms are configured to engage an outer surface of the spinal implant.

The proximal adjustment assembly of the spinal implant may include a linkage body pivotably coupled to the upper and lower bodies. The linkage body may have proximal cavities defined in lateral sides thereof, and each connector arm of the insertion instrument may include an engagement feature radially movable relative to the longitudinal axis such that the engagement features are movable in and out of engagement with the proximal cavities of the spinal implant.

In embodiments, each engagement feature is disposed on a distal portion of the respective connector arm and the connector assembly includes connector plates slidably disposed over the connector arms. When the connector plates are disposed in a proximal position, the distal portions of the connector arms extend radially outwardly relative to the longitudinal axis and when the connector plates are disposed in a distal position, the distal portions of the connector arms are substantially aligned with the longitudinal axis.

In some embodiments, the body portion of the insertion instrument includes elongated rails slidably disposed on the opposed sides of the elongated shaft. The elongated rails are coupled to the connector plates of the connector assembly such that longitudinal movement of the elongated rails causes a corresponding longitudinal movement of the connector plates between the proximal and distal positions. In certain embodiments, the body portion of the insertion instrument includes a rotation knob threadably engaged with a proximal portion of the elongated shaft and coupled to proximal ends of the elongated rails such that rotation of the rotation knob causes longitudinal movement of the elongated rails.

The system may further include a driving instrument and/or a set screw driver positionable through a lumen defined through the insertion instrument. The driving instrument may be configured to actuate the proximal and distal adjustment assemblies. The set screw driver may be configured to engage a set screw with the spinal implant to lock a position of the spinal implant.

In accordance with yet another aspect of the present disclosure, a system includes a spinal implant and a driving instrument. The spinal implant has a proximal region and a distal region, and includes an upper body, a lower body, a proximal adjustment assembly, and a distal adjustment assembly. Each of the upper and lower bodies includes an outer surface and an inner surface, and the inner surfaces of the upper and lower bodies are disposed in opposed relation relative to each other. The proximal adjustment assembly is disposed between the upper and lower bodies in the proximal region of the spinal implant and is adjustably coupled to the upper and lower bodies. The distal adjustment assembly is disposed between the upper and lower bodies in the distal region of the spinal implant and is adjustably coupled to the upper and lower bodies. The proximal and distal adjustment assemblies are independently movable, both concurrently and alternately, to change a vertical height of at least one of the proximal region or the distal region of the spinal implant. The driving instrument includes an outer shaft including a distal end configured to actuate the proximal adjustment assembly, a distal inner shaft disposed within the outer shaft and including a distal end configured to actuate the distal adjustment assembly, and a proximal shaft assembly. The proximal shaft assembly includes a proximal outer shaft, a proximal inner shaft disposed within the proximal outer shaft, and an adjustment knob for adjusting the position of the proximal inner shaft relative to the proximal outer shaft. A distal portion of the proximal outer shaft is disposed within a proximal portion of the distal inner shaft, and the adjustment knob is movable between a height position configured to allow for simultaneous actuation of the proximal and distal adjustment assemblies, a proximal position configured to allow for actuation of only the proximal adjustment assembly and a distal position configured to allow for actuation of only the distal adjustment assembly.

The proximal adjustment assembly of the spinal implant may include a flange nut that is longitudinally movable to drive a change in the vertical height of the proximal region of the spinal implant, and the distal adjustment assembly of the spinal implant may include a threaded post that is longitudinally movable to drive a change in the vertical height of the distal region of the spinal implant. The flange nut may include a threaded opening defined therethrough that is threadably engaged with the threaded post.

In embodiments, the outer shaft of the driving instrument includes an open distal tip having an inner surface configured to engage an outer surface of the flange nut, and the distal inner shaft of the driving instrument including a distal tip configured to engage a recessed proximal end of the threaded post.

In accordance with another aspect of the present disclosure, a method of implanting a spinal implant into a disc space between adjacent vertebral bodies includes: inserting a spinal implant that is releasably attached to a distal end of an insertion instrument into a disc space; inserting a driving instrument into a lumen defined through the insertion instrument and into engagement with the spinal implant; and adjusting at least one of the proximal or distal adjustment assemblies of the spinal implant with the driving instrument. The spinal implant includes an upper body, a lower body, a proximal adjustment assembly, and a distal adjustment assembly. Each of the upper and lower bodies includes an outer surface and an inner surface, and the inner surfaces of the upper and lower bodies are disposed in opposed relation relative to each other. The proximal adjustment assembly is disposed between the upper and lower bodies in the proximal region of the spinal implant and is adjustably coupled to the upper and lower bodies. The distal adjustment assembly is disposed between the upper and lower bodies in the distal region of the spinal implant and is adjustably coupled to the upper and lower bodies. The proximal and distal adjustment assemblies are independently movable, both concurrently and alternately, to change a vertical height of at least one of the proximal region or the distal region of the spinal implant. The driving instrument includes an outer shaft including a distal end configured to actuate the proximal adjustment assembly, a distal inner shaft disposed within the outer shaft and including a distal end configured to actuate the distal adjustment assembly, and a proximal shaft assembly. The proximal shaft assembly includes a proximal outer shaft, a proximal inner shaft disposed within the proximal outer shaft, and an adjustment knob for adjusting the position of the proximal inner shaft relative to the proximal outer shaft. A distal portion of the proximal outer shaft is disposed within a proximal portion of the distal inner shaft, and the adjustment knob is movable between a height position configured to allow for simultaneous actuation of the proximal and distal adjustment assemblies, a proximal position configured to allow for actuation of only the proximal adjustment assembly and a distal position configured to allow for actuation of only the distal adjustment assembly.

The method may further include attaching the spinal implant to the distal end of the insertion instrument with the outer surfaces of the upper and lower bodies substantially parallel to each other. The method may further include locking the position of the spinal implant with a set screw. The may further include adjusting the vertical height of at least one of the proximal or distal regions of the spinal implant prior to inserting the spinal implant into the disc space.

In embodiments, adjusting at least one of the proximal or distal adjustment assemblies includes setting the driving instrument to the height position to actuate both the proximal and distal adjustment assemblies such that the upper and lower bodies of the spinal implant are expanded while maintaining the upper and lower bodies in substantially parallel relation to each other until the spinal implant engages the vertebral bodies. In some embodiments, the method further includes individually actuating at least one of the proximal or distal adjustment assemblies to adjust the height of at least one of the proximal or distal regions of the spinal implant to accommodate lordosis. In certain embodiments, adjusting at least one of the proximal or distal adjustment assemblies includes setting the driving instrument to the proximal or distal position to individually actuate the proximal or distal adjustment assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 9A is an end view of the spinal implant of FIG. 1, with a distal region of the spinal implant fully expanded;

FIG. 9B is a side cross-sectional view of the spinal implant of FIG. 9A, taken along line 9B-9B of FIG. 9A;

FIG. 11A is an end view of the spinal implant of FIG. 1, with a proximal region of the spinal implant fully expanded;

FIG. 11B is a side cross-sectional view of the spinal implant of FIG. 11A, taken along line 11B-11B of FIG. 11A;

FIG. 18A is a side view of the system of FIG. 17;

FIG. 18B is a top cross-sectional view of the system of FIGS. 17 and 18A, taken along line 18B-18B of FIG. 18A;

FIG. 19A is a perspective view of the system of FIG. 17, with the insertion instrument in an open position and the spinal implant aligned with the insertion instrument;

FIG. 19B is a close-up view of the area of detail indicated in FIG. 19A;

FIG. 20A is a perspective view of the system of FIG. 17, with the insertion instrument in a closed position and the spinal implant releasably secured to the insertion instrument;

FIG. 20B is a close-up view of the area of detail indicated in FIG. 20A;

FIG. 25A is a side view of the driving instrument of FIGS. 21 and 22, in a posterior position;

FIG. 25B is a cross-sectional view of the driving instrument of FIG. 25A, taken along line 25B-25B of FIG. 25A;

FIG. 28A is a side view of the system of FIG. 27, with the driving instrument in an anterior position;

FIG. 28B is a cross-sectional view of the system of FIG. 28A, taken along line 28B-28B of FIG. 28A;

FIG. 29A is a side view of the system of FIG. 27, with the driving instrument in a posterior position;

FIG. 29B is a cross-sectional view of the system of FIG. 29A, taken along line 29B-29B of FIG. 29A;

DETAILED DESCRIPTION

Figure 1:
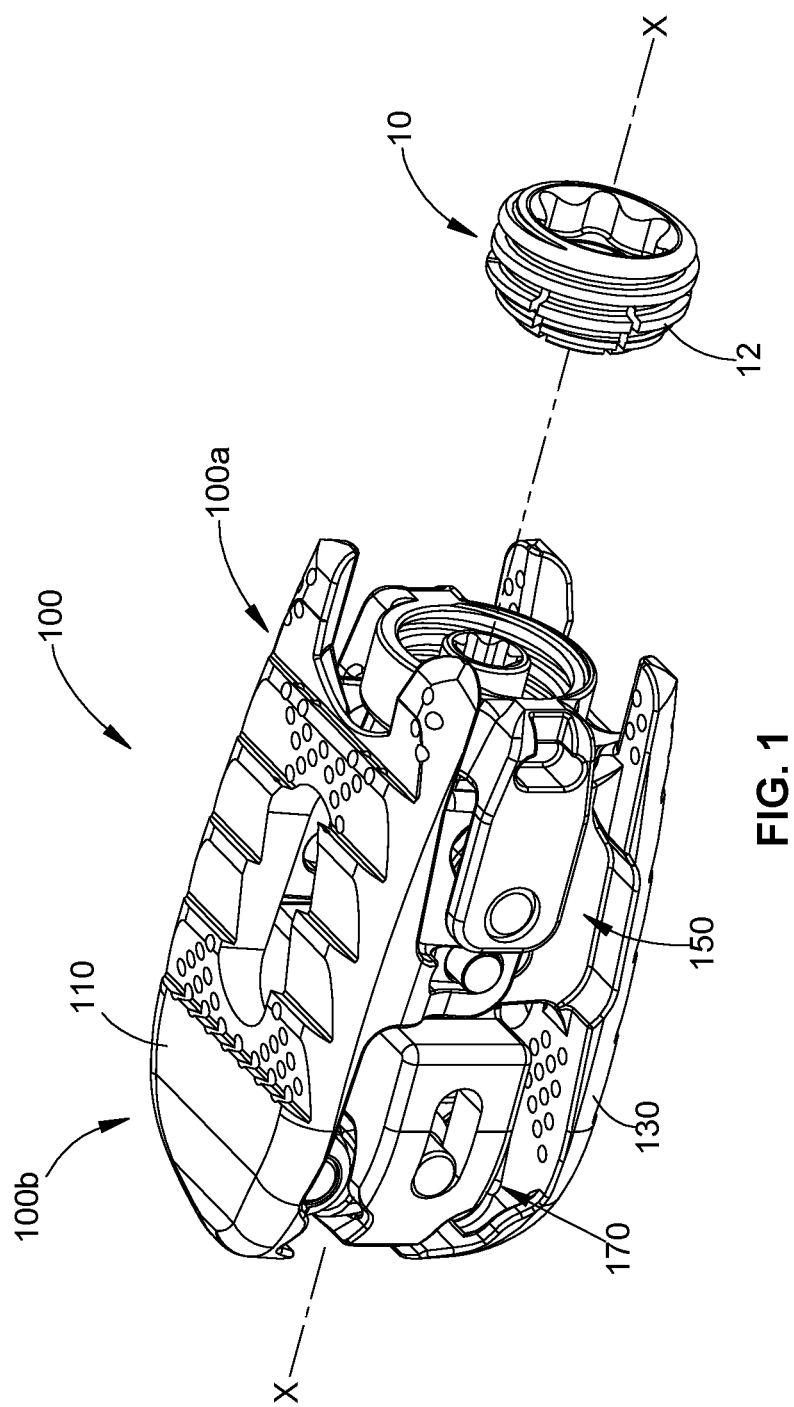
FIG. 1 is a perspective view, with parts separated, of a spinal implant and a set screw in accordance with an embodiment of the present disclosure.

Embodiments of the present disclosure are now described in detail with reference to the drawings in which like reference numerals designate identical or corresponding elements in each of the several views. The term "clinician" refers to a doctor (e.g., a surgeon), a nurse, or any other care provider, and may include support personnel. Throughout this description, the term "proximal" refers to a portion of a system, device, or component thereof that is closer to a clinician, and the term "distal" refers to the portion of the system, device, or component thereof that is farther from the clinician.

Referring now to the drawings, FIG. 1 illustrates an expandable spinal implant or a spinal implant 100 in accordance with an embodiment of the present disclosure. Spinal implant 100 has a proximal region 100a and a distal region 100b extending along a longitudinal axis "X." The spinal implant 100 includes an upper body 110 and a lower body 130 disposed in opposed relation relative to each other and coupled together by a proximal adjustment assembly 150 and a distal adjustment assembly 170. The proximal and distal adjustment assemblies 150, 170 are independently movable to allow for adjustment in the angular relationship and vertical distance between the upper and lower bodies 110, 130 of the proximal and distal regions 100a, 100b of the spinal implant 100. Accordingly, the spinal implant 100 is movable between a collapsed configuration and a fully expanded configuration, and includes a number of partially expanded configurations, as described in further detail below. The desired configuration of the spinal implant 100 may be locked in place via a set screw 10 that is engageable with the proximal and distal adjustment assemblies 150, 170, as also described in further detail below.

Figure 2:
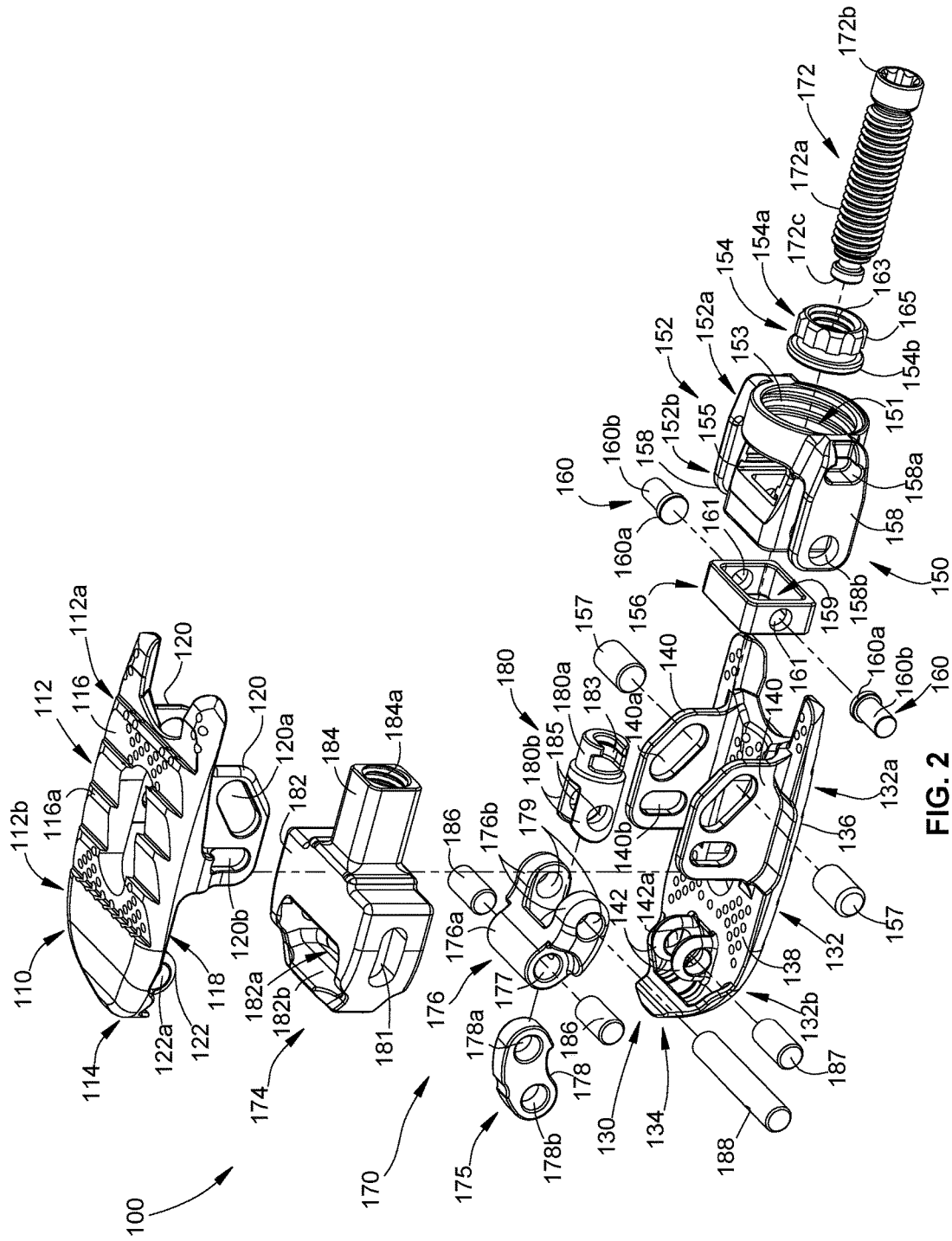
FIG. 2 is an exploded view of the spinal implant of FIG. 1.

Turning now to FIG. 2, the upper body 110 of the spinal implant 100 includes an elongated substantially planar portion 112 having a proximal portion 112a, a distal portion 112b, and a curved portion 114 disposed distally of the planar portion 112. An outer surface 116 of the planar portion 112 includes a plurality of retaining features 116a in the form of tapered ridges. In embodiments, the tapered ridges may be formed by 3D printing to produce customized structures. The plurality of retaining features 116a are configured to frictionally engage an adjacent surface of a vertebral body (e.g., a vertebral endplate) to maintain the position of the spinal implant 100 relative to the vertebral body and/or to inhibit the spinal implant 100 from backing out of the intervertebral space as the plurality of retaining features 116a may bite into the vertebral endplate. It should be understood that the plurality of retaining features 116a may have other ridge configurations, or may be protrusions, bumps, teeth, or other texturized structures within the purview of those skilled in the art. It should further be understood that the plurality of retaining features 116a may be formed by other processes (e.g., etching or molding techniques) within the purview of those skilled in the art.

An inner surface 118 of the upper body 110 includes a pair of proximal fins 120 extending from the proximal portion 112a of the planar portion 112 and a pair of distal posts 122 extending from the distal portion 112b of the planar portion 112 proximate to the curved portion 114. Each proximal fin 120 includes an angled slot 120a and a vertical slot 120b defined therein that are opposed and aligned with the respective angled and vertical slots 120a, 120b of the other proximal fin 120. The angled slot 120a is disposed proximal to the vertical slot 120b. Each distal post 122 includes a through hole 122a defined therethrough that are opposed and aligned with each other. It should be understood that the proximal fin 120 and the distal post 122 that are not fully shown are identical to the proximal fin 120 and the distal post 122 shown, and similar to the proximal fins 140 and the distal posts 142 of the lower body 130, as described in further detail below.

Figure 6A:
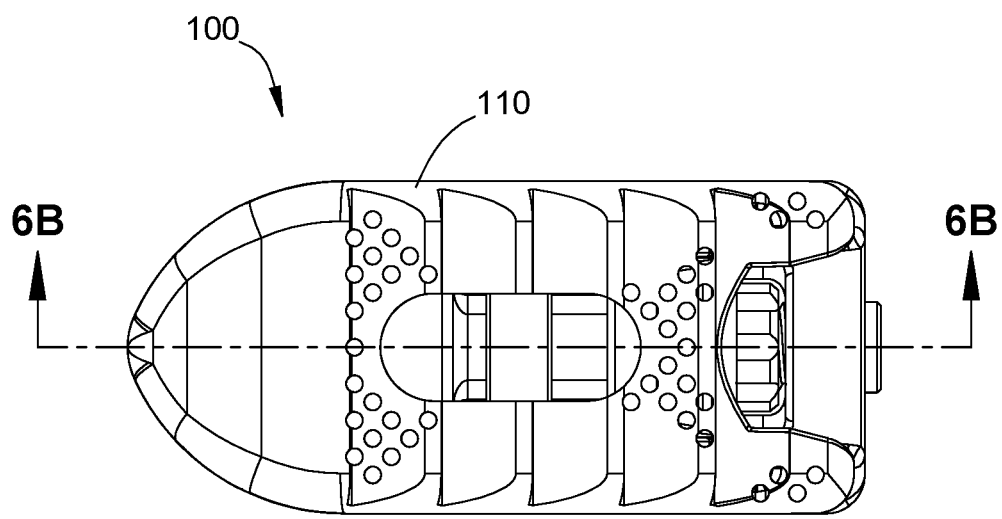
FIG. 6A is a top view of the spinal implant of FIG. 1, in a collapsed position.
Figure 6B:
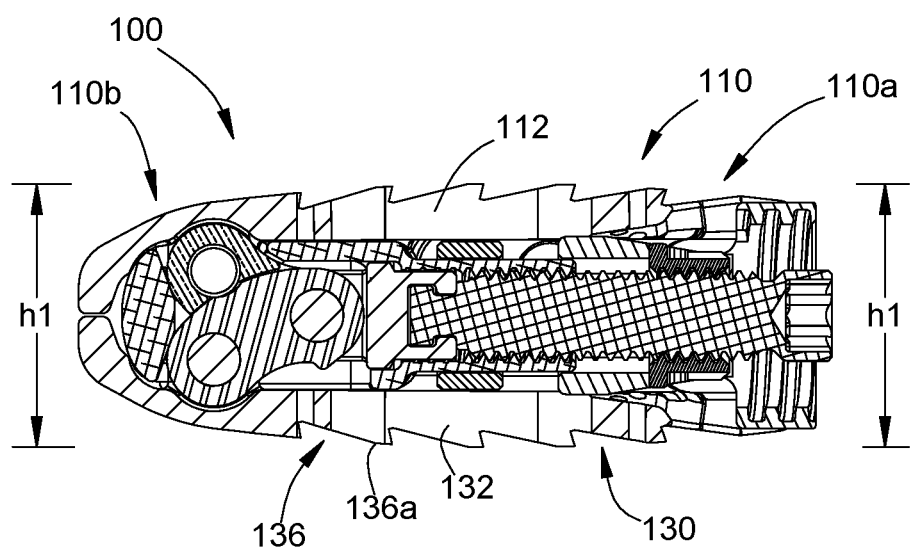
FIG. 6B is a cross-sectional view of the spinal implant of FIG. 6A, taken along line 6B-6B of FIG. 6A.
Figure 7A:
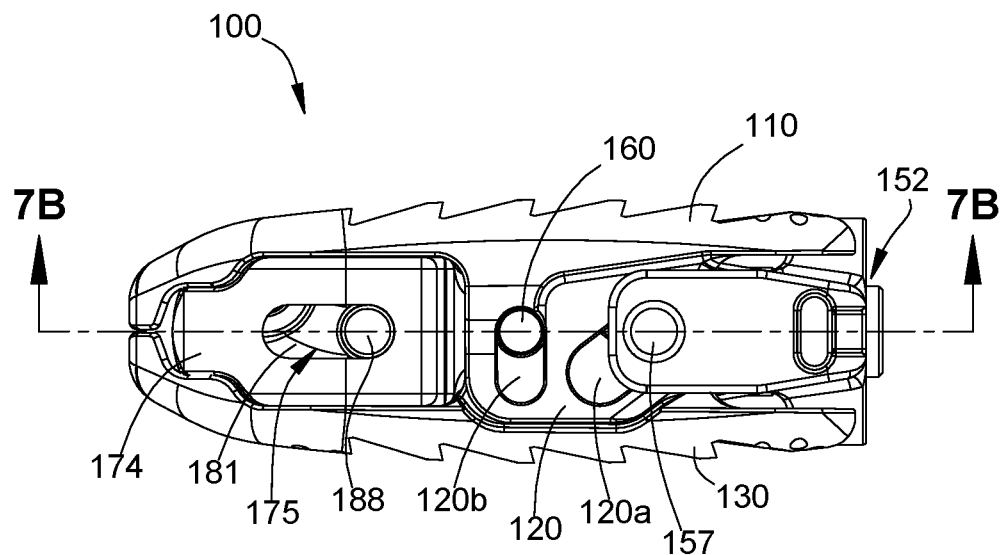
FIG. 7A is a side view of the spinal implant of FIGS. 6A and 6B.
Figure 7B:
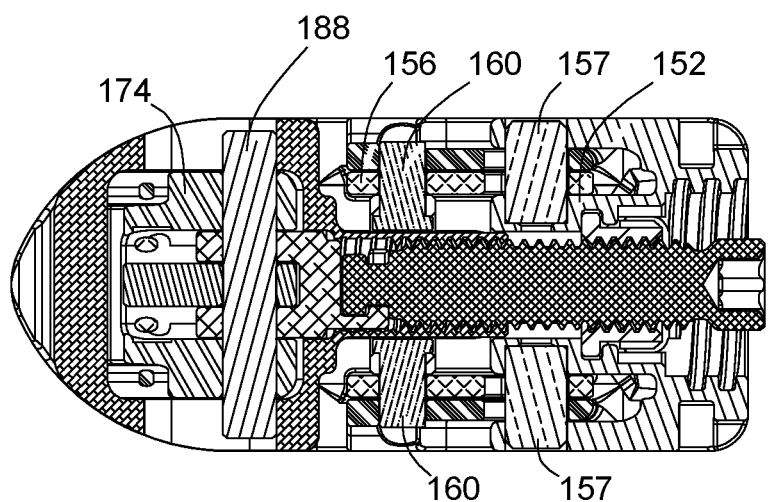
FIG. 7B is a top cross-sectional view of the spinal implant of FIGS. 6A-7A, taken along line 7B-7B of FIG. 7A.
Figure 8B:
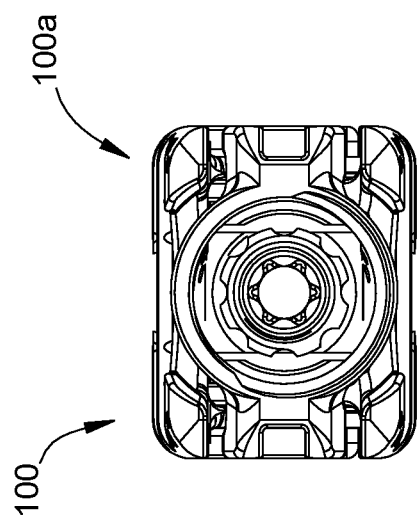
FIGS. 8A and 8B are end views of the spinal implant of FIGS. 6A-7B.
Figure 8A:
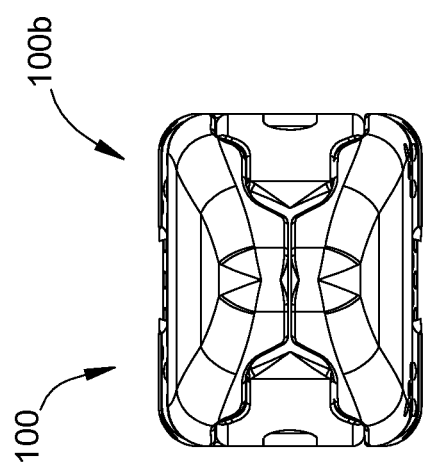

The lower body 130 includes an elongated substantially planar portion 132 having a proximal portion 132a and a distal portion 132b, and a curved portion 134 disposed distally of the planar portion 132. The planar portion 132 includes an outer surface 136 having a plurality of retaining features 136a (FIG. 6B) disposed thereon that are configured to frictionally engage an adjacent surface of a vertebral body as discussed above with regard to the plurality of retaining features 116a of the upper body 110. An inner surface 138 of the lower body 130 includes a pair of proximal fins 140 extending from the proximal portion 132a of the planar portion 132, and a pair of distal posts 142 extending from the distal portion 132b of the planar portion 132 proximal of the curved portion 134. Each proximal fin 140 includes an angled slot 140a and a vertical slot 140b defined therein that are opposed and aligned with the respective angled and vertical slots 140a, 140b of the other proximal fin 140. Each distal post 142 includes a through hole 142a defined therethrough that are opposed and aligned with each other.

The proximal adjustment assembly 150 includes a linkage body 152, a flange nut 154 positionable within the linkage body 152, and a coupler 156 disposed distally of the linkage body 152. The linkage body 152 includes a proximal portion 152a and a distal portion 152b, and defines a central opening 151 therethrough, The proximal portion 152a of the linkage body 152 includes a threaded inner surface 153 configured to mate with a threaded outer surface 12 (FIG. 1) of the set screw 10. The distal portion 152b of the linkage body 152b includes a recess 155 defined between a pair of arms 158 extending along lateral sides of the linkage body 152. The arms 158 include proximal cavities 158a that are dimensioned to engage an insertion instrument 200 (see e.g. FIG. 17) and distal holes 158b that are aligned with the angled slots 120a, 140a of the proximal fins 120, 140 of the upper and lower bodies 110, 130.

Figure 3A:
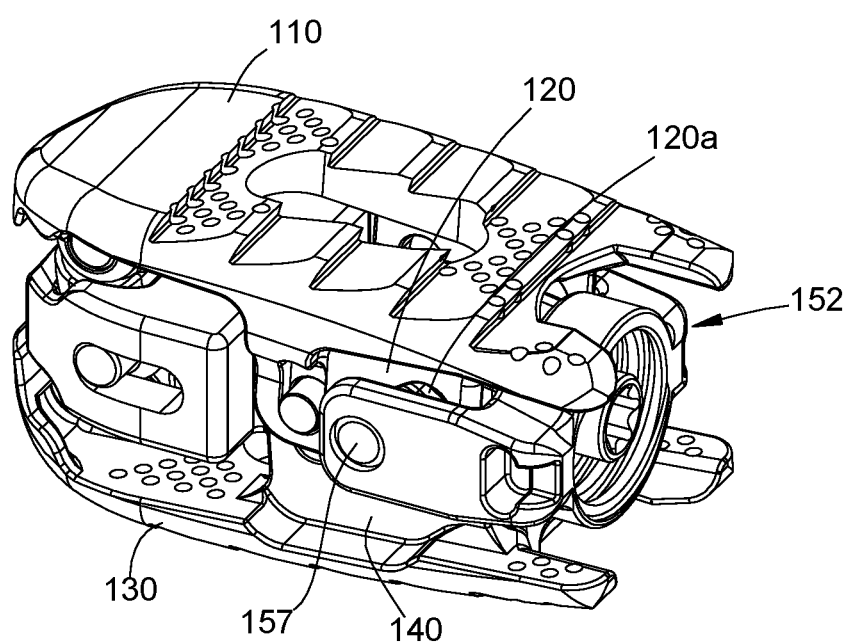
FIG. 3A is a perspective view of the spinal implant of FIG. 1, with the set screw removed.
Figure 3B:
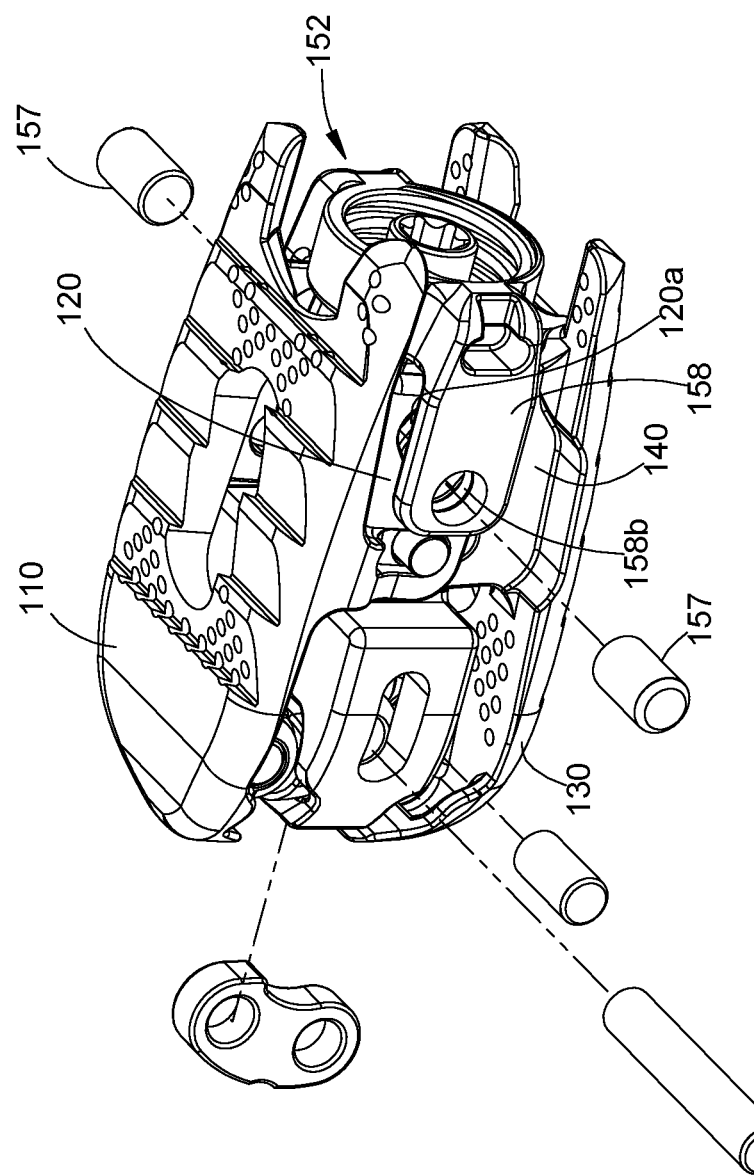
FIG. 3B is a perspective view of the spinal implant of FIG. 3A, with pivot pins separated.

As shown in FIGS. 3A and 3B, in conjunction with FIG. 2, a first set of pins 157 respectively extends through and frictionally engages the distal holes 158b of the linkage body 152 and the angled slots 120a, 140a of the proximal fins 120, 140 of the upper and lower bodies 110, 130 to adjustably couple the upper and lower bodies 110, 130 together via the linkage body 152. The first set of pins 157 is configured to ride along the angled slots 120a, 140a of the proximal fins 120, 140 of the upper and lower bodies 110, 130 as the linkage body 152 is moved proximally and/or distally between the upper and lower bodies 110, 130.

Figure 4A:
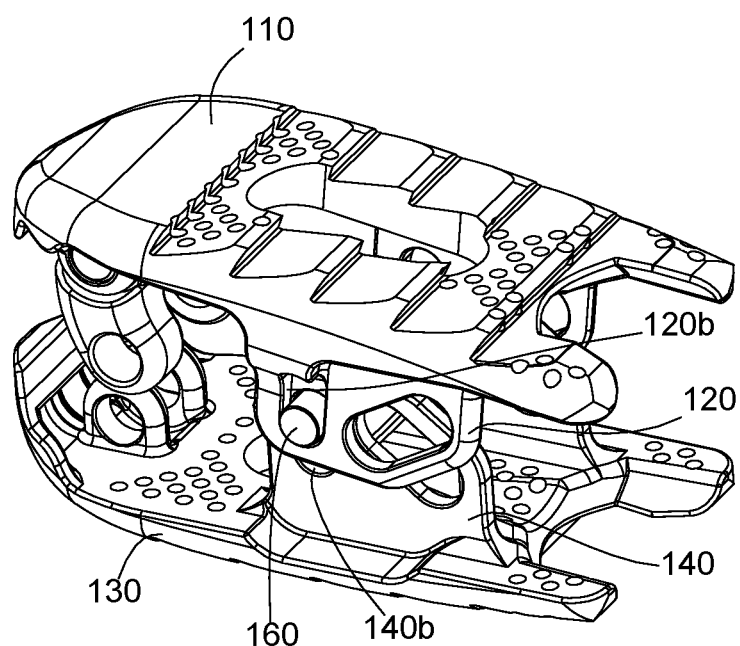
FIG. 4A is a perspective view of the spinal implant of FIG. 1, with adjustment assemblies removed.
Figure 4B:
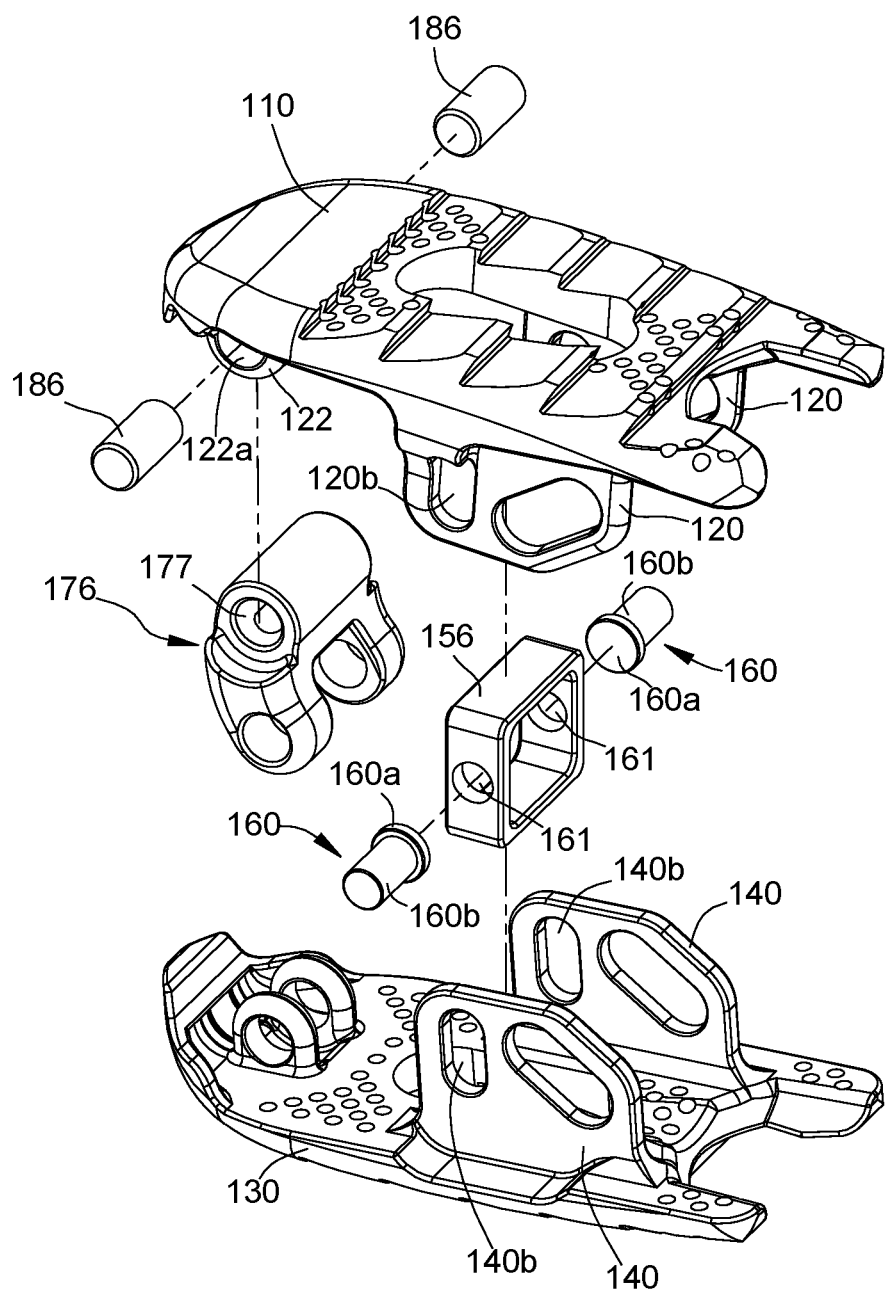
FIG. 4B is an exploded perspective view of the spinal implant of FIG. 4A, with parts separated.

With continued reference to FIG. 2, the coupler 156 includes a central opening 159 defined therein that is aligned with the central opening 151 of the linkage body 152. The central openings 151, 159 of the linkage body 152 and the coupler 156 are sized and shaped to engage, and be supported on, a shaft 184 of an expander 174 of the distal adjustment assembly 170. As shown in FIGS. 4A and 4B, in conjunction with FIG. 2, nubs 160 have flanged inner ends 160a that are dimensioned to be retained within the coupler 156 such that elongate bodies 160b of the nubs 160 extend laterally through side openings 161 of the coupler 156 and slide within the vertical slots 120b, 140b of the proximal fins 120, 140 of the upper and lower bodies 110, 130.

Figure 5A:
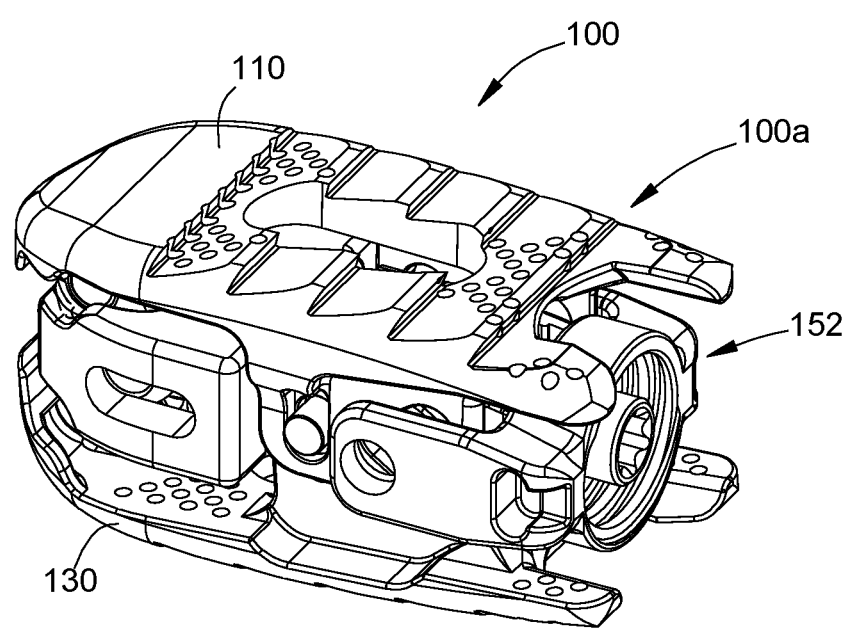
FIG. 5A is a perspective view of the spinal implant of FIG. 1, with parts removed.
Figure 5B:
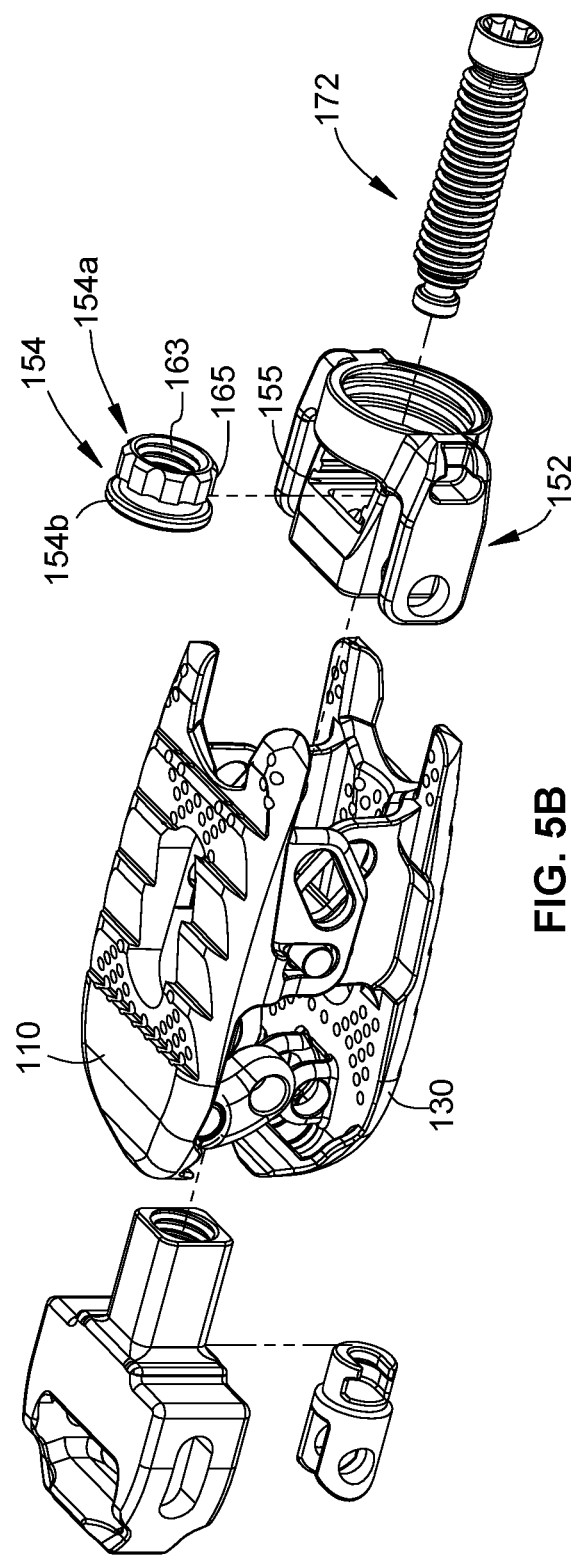
FIG. 5B is a perspective view of the spinal implant of FIG. 5A, with parts separated.

As shown in FIGS. 5A and 5B, in conjunction with FIG. 2, the flange nut 154 includes a proximal portion 154a and a flanged distal portion 154b. The proximal portion 154a includes a threaded opening 163 defined therethrough that is configured to threadably engage a threaded post 172 of the distal adjustment assembly 170, and a shaped outer surface 165 that is configured to mate with a driving instrument 300 (see e.g., FIG. 21) such that either the flange nut 154 or the threaded post 172 may be rotated and axially translated with respect to the other. The flanged distal portion 154b is dimensioned to be received within the recess 155 of the linkage body 152. Accordingly, movement of the flange nut 154 distally moves the linkage body 152 distally causing the first set of pins 157 to translate within the angled slots 120a, 140a of the proximal fins 120, 140 and the nubs 160 of the coupler 156 to translate within the vertical slots 120b, 140b of the proximal fins 120, 140 to increase the distance between the upper and lower bodies 110 and 130 in the proximal region 100a of the spinal implant 100. Conversely, movement of the flange nut 154 proximally moves the linkage body 152 proximally to reduce the distance between the upper and lower bodies 110, 130 in the proximal region 100a of the spinal implant 100.

Referring again to FIG. 2, the distal adjustment assembly 170 includes the threaded post 172, an expander 174, and a pivot linkage assembly 175 including an upper pivot linkage 176, a lower pivot linkage 178, and a connector linkage 180. The threaded post 172 includes an elongated threaded body 172a having a recessed proximal end 172b configured to mate with a driving instrument 300 (see e.g., FIG. 21) and a distal end 172c. The recessed proximal end 172b may have a hex feature, e.g., hexagonal or hexolobular in shape, or any other suitable configuration that is engageable with a suitable driving instrument to enable the driving instrument to control the insertion and/or advancement, as well as retraction and/or withdrawal, of the threaded post 172 within the spinal implant 100.

The expander 174 includes a body portion 182 defining a cavity 182a therein. A pair of opposed longitudinal slots 181 is disposed on lateral sides of the body portion 182, and a distal end of the body portion 182 includes a double ramped inner surface 182b (see e.g., FIG. 9B). A shaft 184 extends proximally from the body portion 182 of the expander 174 and defines a threaded opening 184a therein that is configured to threadably engage the elongated threaded body 172a of the threaded post 172.

The pivot linkage assembly 175 includes an upper pivot linkage 176 having an upper body 176a defining an upper hole 177 therethrough and lower legs 176b extending from the upper body 176a, each of the lower legs 176b including a lower hole 179 defined therethrough. The pivot linkage assembly 175 further includes a lower pivot linkage 178 having an upper hole 178a and a lower hole 178b defined therethrough, and a connector linkage 180 including a proximal body 180a defining a recess 183 therein and distal legs 180b extending from the proximal body 180a, each of the distal legs 180b defining a distal hole 185 therethrough.

As shown in FIGS. 2 and 4B, the upper hole 177 of the upper pivot linkage 176 is aligned with the through holes 122a defined in the distal posts 122 of the upper body 110, and a second set of pins 186 is inserted therethrough for pivotably connecting the upper pivot linkage 176 with the upper body 110. It is contemplated that a single pin could be used to pivotably connect the upper pivot linkage 176 with the upper body 110. With continued reference to FIG. 2, the lower hole 178b of the lower pivot linkage 178 is aligned with the through holes 142a defined in the distal posts 142 of the lower body 130, and a pin 187 is inserted therethrough for pivotably connecting the lower pivot linkage 178 with the lower body 130. The lower holes 179 of the upper pivot linkage 176, the upper hole 178a of the lower pivot linkage 178, and the distal holes 185 of the connector linkage 180 are aligned with each other and with the longitudinal slots 181 defined in the expander 174 such that the upper pivot linkage 176, the lower pivot linkage 178, and the connector linkage 180 are disposed within the cavity 182a in the body portion 182 of the expander 174, and a pin 188 is disposed therethrough for pivotably securing the upper and lower bodies 110 and 130 to the expander 174 of the distal adjustment assembly 170 via the pivot linkage assembly 175. The recess 183 of the connector linkage 180 is configured to receive the distal end 172c of the threaded post 172 therein to prevent the threaded post 172 from being removed from the spinal implant 100 during proximal movement thereof. This arrangement allows for simultaneous translation of the pin 188 within the longitudinal slots 181 of the expander 174 and pivoting movement of the upper and lower pivot linkages 176, 178 during longitudinal translation of the threaded post 172.

In use, the threaded post 172 is rotated in a first direction to advance the threaded post 172 distally which pushes the connector linkage 180 distally and drives the upper and lower pivot linkages 176, 178 against the double ramped inner surface 182b of the expander 174 thereby increasing the height between the upper and lower bodies 110, 130 at the distal region 100b of the spinal implant 100. Rotation of the threaded post 172 in a second, reverse direction moves the threaded post 172 proximally which, in turn, moves the connector linkage 180 proximally to allow the upper and lower pivot linkages 176, 178 to collapse, thereby decreasing the height between the upper and lower bodies 110, 130 at the distal region 100b of the spinal implant 100.

Accordingly, the upper and lower pivot linkages 176, 178 are coupled to the upper and lower bodies 110, 130, and are pivotable relative to each other about the pin 188 to change the distance between the upper and lower bodies 110, 130, and thus, the angular position and vertical height of the spinal implant 100 about the distal region 100b of the spinal implant 100. Thus, the proximal and distal regions 100a and 100b of the spinal implant 100 are independently movable with respect to each other via the proximal and distal adjustment assemblies 150, 170 so that the spinal implant 100 may have a variety of configurations.

The independent adjustability of the proximal and distal regions 100a, 100b of the spinal implant 100 allows a clinician to adjust the dimensions of the spinal implant 100 (i.e., vertical heights of the proximal and distal regions) such that the spinal implant 100 can be inserted between two vertebrae with relatively narrow access in an unexpanded position, without force, to avoid trauma to the vertebral bodies, and in particular, the endplates of the vertebral bodies. The proximal and/or distal regions 100a, 100b of the spinal implant 100 can then be adjusted to partially or fully expanded positions so that the upper and lower bodies 110, 130 are aligned with the endplates to maximize surface contact between the spinal implant 100 and the endplates, and to match the dimensions of the disc space defined between the endplates in which the spinal implant 100 is disposed. The adjustability of the spinal implant 100 allows a clinician, for example, to minimize trauma to the vertebrae during implantation of the spinal implant 100, to tailor the spinal implant 100 to conform to the anatomy of individual patients, to maximize contact between the spinal implant 100 and the endplates to create bone growth, to match the natural disc height of the disc space, to obtain a desired amount of lordosis for the spine, to improve the seating of the spinal implant 100 within the disc space, and/or to lessen the likelihood of expulsion of the spinal implant 100 from the disc space.

Referring now to FIGS. 6A-8B, the spinal implant 100 has a collapsed, or unexpanded, position. In the collapsed position, the planar portions 112, 132 of the upper and lower bodies 110, 130 are disposed in parallel relationship to each other. As specifically shown in FIG. 6B, each of the proximal and distal regions 100a, 100b of the spinal implant 100 has a height, "h1", that defines the minimum distance at which the upper and lower bodies 110, 130 may be positioned relative to each other. In embodiments, the height "h1" may range from about 3 mm to about 18 mm, and in some embodiments, the height "h1" is from about 8 mm to about 13 mm. As shown in FIGS. 7A and 7B, the first set of pins 157 of the linkage body 152 and the nubs 160 of the coupler 156 are disposed within the angled slots 120a, 140a and the vertical slots 120b, 140b, respectively, of the proximal fins 120, 140 of the upper and lower bodies 110, 130 such that the first set of pins 157 and the nubs 160 respectively rest within uppermost portions of the angled slots 120a, 140a and the vertical slots 120b, 140b of the upper and lower bodies 110, 130. The pin 188, which is disposed through the expander 174 and the pivot linkage assembly 175, is disposed in a proximalmost position within the longitudinal slots 181 of the expander 174.

Figure 10:
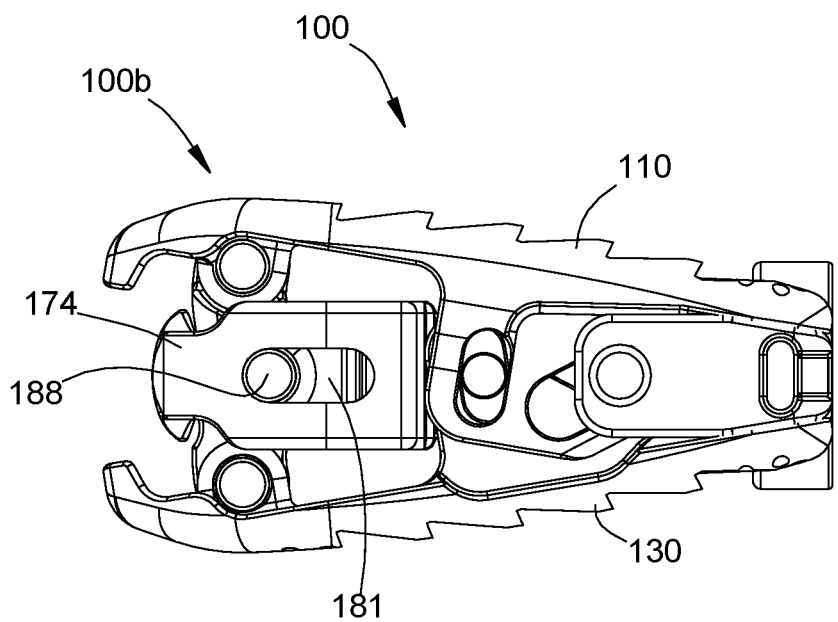
FIG. 10 is a side view of the spinal implant of FIGS. 9A and 9B.

As shown in FIGS. 9A-10, the threaded post 172 may be moved proximally and distally to change the distance between the upper and lower bodies 110, 130 in the distal region 100b of the spinal implant 100. Rotation of the threaded post 172 in a first direction moves the threaded post 172 distally through the threaded opening 163 of the flange nut 154 and the threaded opening 184a of the shaft 184 of the expander 174 which, in turn, moves the connector linkage 180 distally which, in turn, pushes the upper and lower pivot linkages 176, 178 into the double ramped inner surface 182b of the expander 174 to change the distance between the upper and lower bodies 110, 130 in the distal region 100b of the spinal implant 100. As specifically shown in FIG. 9B, the distal region 110b of the spinal implant 100 has a height, "h2", that defines the maximum distance at which the upper and lower bodies, 110, 130 may be positioned relative to each other in the distal region 110b of the spinal implant 100. In embodiments, the height "h2" may range from about 5 mm to about 22 mm, and in some embodiments, the height "h2" is from about 10 mm to about 15 mm. As specifically shown in FIG. 10, when the distal region 100b of the spinal implant 100 is fully expanded, the pin 188 is disposed in a distalmost position within the longitudinal slot 181 of the expander 174. It should be understood that the threaded post 172 may be rotated to achieve any of a number of partially expanded positions of the distal region 100b of the spinal implant 100 between heights "h1" and "h2".

Figure 12:
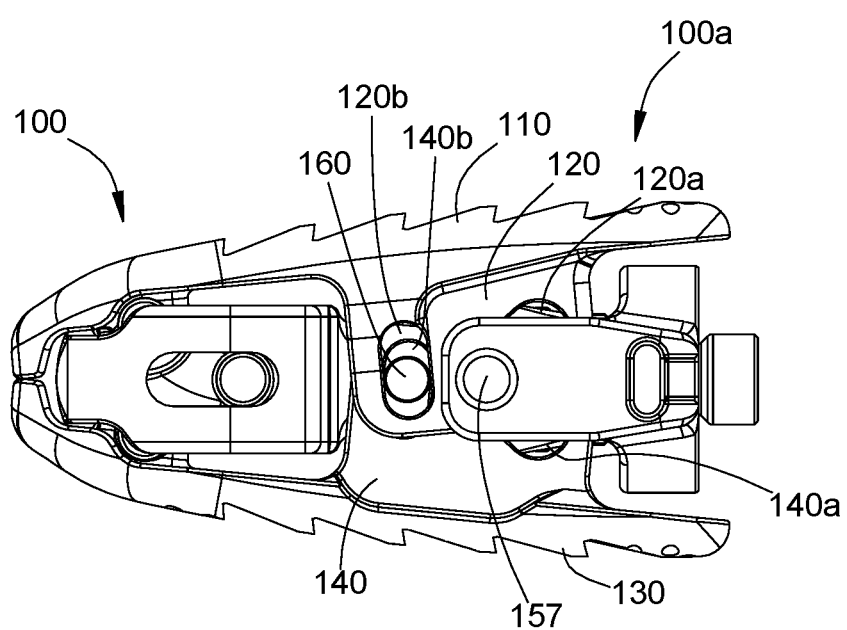
FIG. 12 is a side view of the spinal implant of FIGS. 11A and 11B.

As shown in FIGS. 11A-12, the flange nut 154 may be moved proximally and distally to change the distance between the upper and lower bodies 110, 130 in the proximal region 100a of the spinal implant 100. Rotation of the flange nut 154 in a first direction moves the flange nut 154 and the linkage body 152 distally such that the first set of pins 157 slide within the angled slots 120a, 140a of the proximal fins 120, 140 of the upper and lower bodies 110 and 130, and the nubs 160 of the coupler 156 slide within the vertical slots 120b, 140b of the proximal fins 120, 140 to expand the proximal region 100a of the spinal implant 100. As specifically shown in FIG. 11B, the proximal region 100a of the spinal implant 100 has a height "h3", that defines the maximum distance at which the upper and lower bodies 110, 130 may be positioned relative to each other in the proximal region 110a of the spinal implant 100. In embodiments, the height "h3" may range from about 5 mm to about 22 mm, and in some embodiments, the height "h3" is from about 10 mm to about 15 mm. As specifically shown in FIG. 12, the proximal region 100a of the spinal implant 100 is fully expanded when the first set of pins 157 are disposed within distalmost portions of the angled slots 120a, 140a of the upper and lower bodies 110, 130. It should be understood that the flange nut 154 may be rotated to achieve any number of partially expanded positions of the proximal region 100a of the spinal implant 100 between heights "h1" and "h2".

It is contemplated that the threads on the threaded post 172 may be provided as variable pitch threads over all or a part of the length of the elongated threaded body 172a of the threaded post 172 such that the number of turns required to expand the proximal and/or distal adjustment assemblies 150, 170 is variable, having a fast expansion period along part of the threaded post 172 and a slow or fine expansion period along another part of the threaded post 172. Alternatively, the threads of the threaded post 172 may be double lead threads to provide faster expansion per turn of the threaded post 172.

A person of ordinary skill in the art will readily understand that the proximal and distal regions of the spinal implant may be independently adjusted to achieve a desired configuration of the spinal implant. Accordingly, it is contemplated that only the proximal region or the distal region of the spinal implant may be expanded, should that be a desired configuration, or both the proximal and distal regions of the spinal implant may be expanded (e.g., concurrently or alternately) to achieve a desired configuration (e.g., an implant having a kyphotic shape, a lordotic shape, etc.).

Figure 13A:
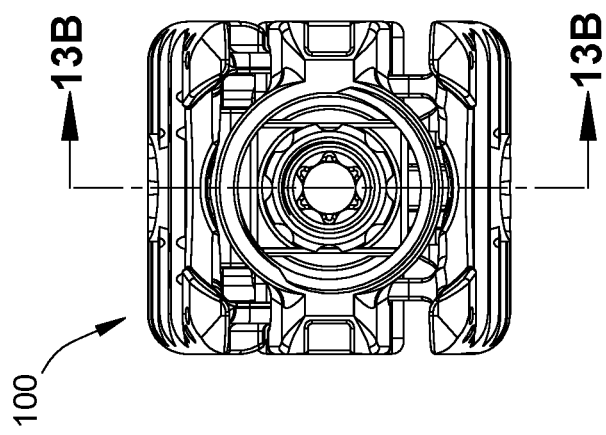
FIG. 13A is an end view of the spinal implant of FIG. 1, with proximal and distal regions of the spinal implant fully expanded.
Figure 13B:
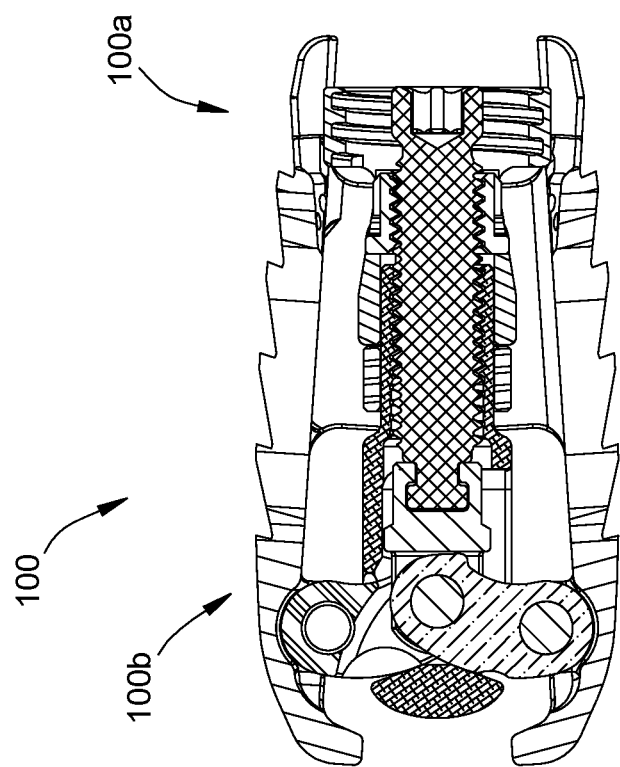
FIG. 13B is a side cross-sectional view of the spinal implant of FIG. 13A, taken along line 13B-13B of FIG. 13A.
Figure 14:
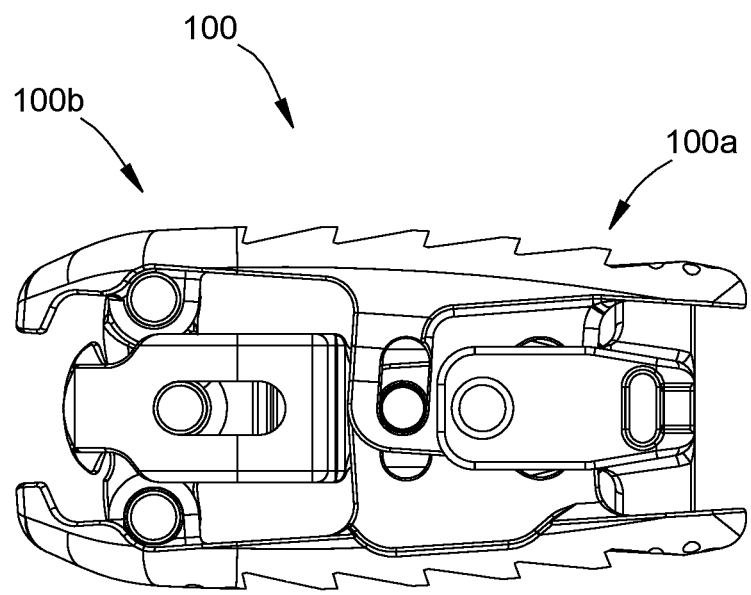
FIG. 14 is a side view of the spinal implant of FIGS. 13A and 13B.
Figure 15:
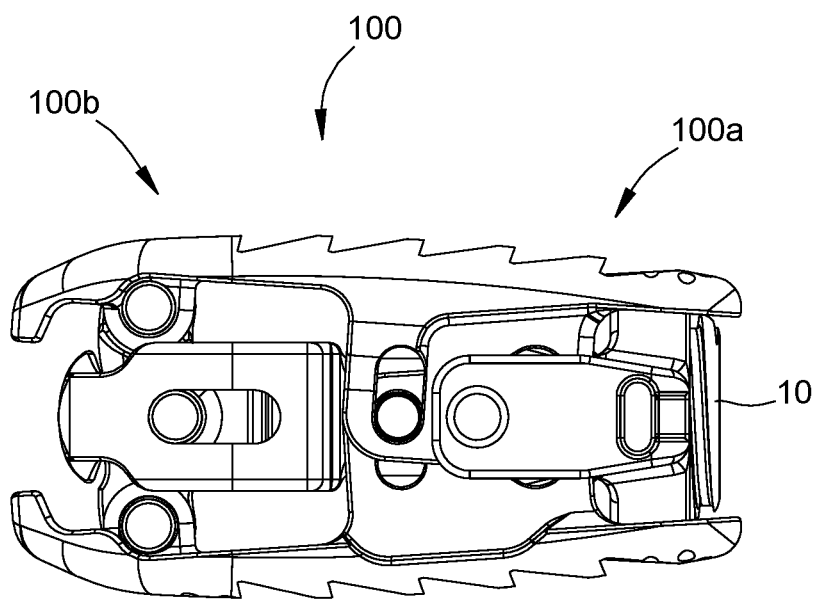
FIG. 15 is a side view of the spinal implant of FIGS. 13A-14 including the set screw of FIG. 1.
Figure 16A:
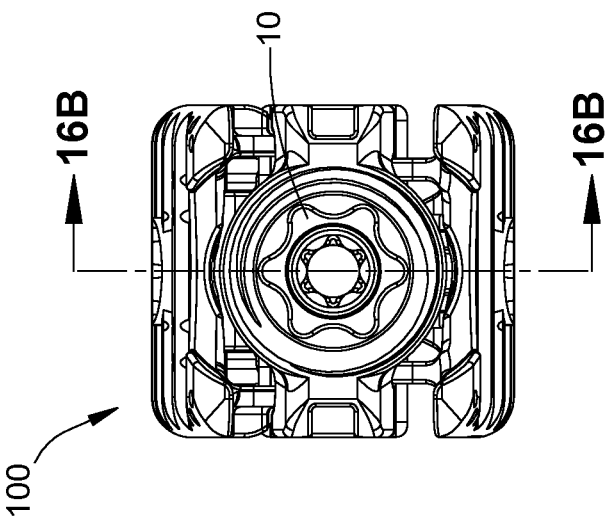
FIG. 16A is an end view of the spinal implant and the set screw of FIG. 15.
Figure 16B:
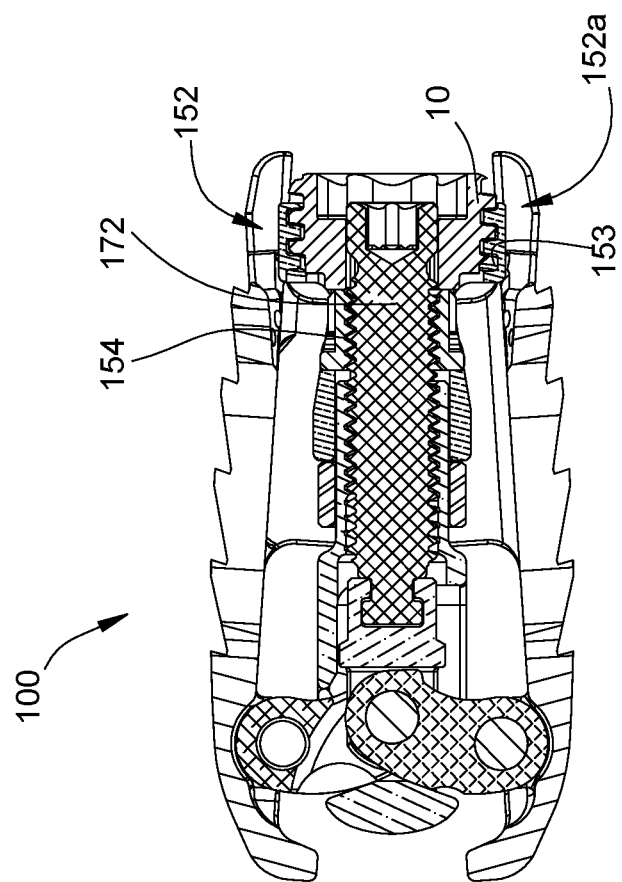
FIG. 16B is a side cross-sectional view of the spinal implant and the set screw of FIGS. 15 and 16A, taken along line 16B-16B of FIG. 16A.

For example, in FIGS. 13A-14, the spinal implant 100 is shown with the proximal and distal regions 100a of the spinal implant 100 each in a fully expanded position. As shown in FIGS. 15-16B, once the desired positions of the proximal and distal regions 100a, 100b of the spinal implant 100 are achieved, the set screw 10 may inserted into the linkage body 152 to lock the position of the spinal implant 100. The set screw 10 engages the threaded inner surface 153 at the proximal portion 152a of the linkage body 152. When so positioned, the set screw 10 blocks the threaded post 172 and the flange nut 154 from moving proximally relative to the linkage body 152, thereby preventing the surgical implant 100 from retracting and collapsing after surgery. Of course, if revision is necessary, the set screw 10 may be removed to access the threaded post 172 and/or the flange nut 154 to collapse the spinal implant 100 for removal or to make further adjustment(s) to the spinal implant 100.

Figure 17:
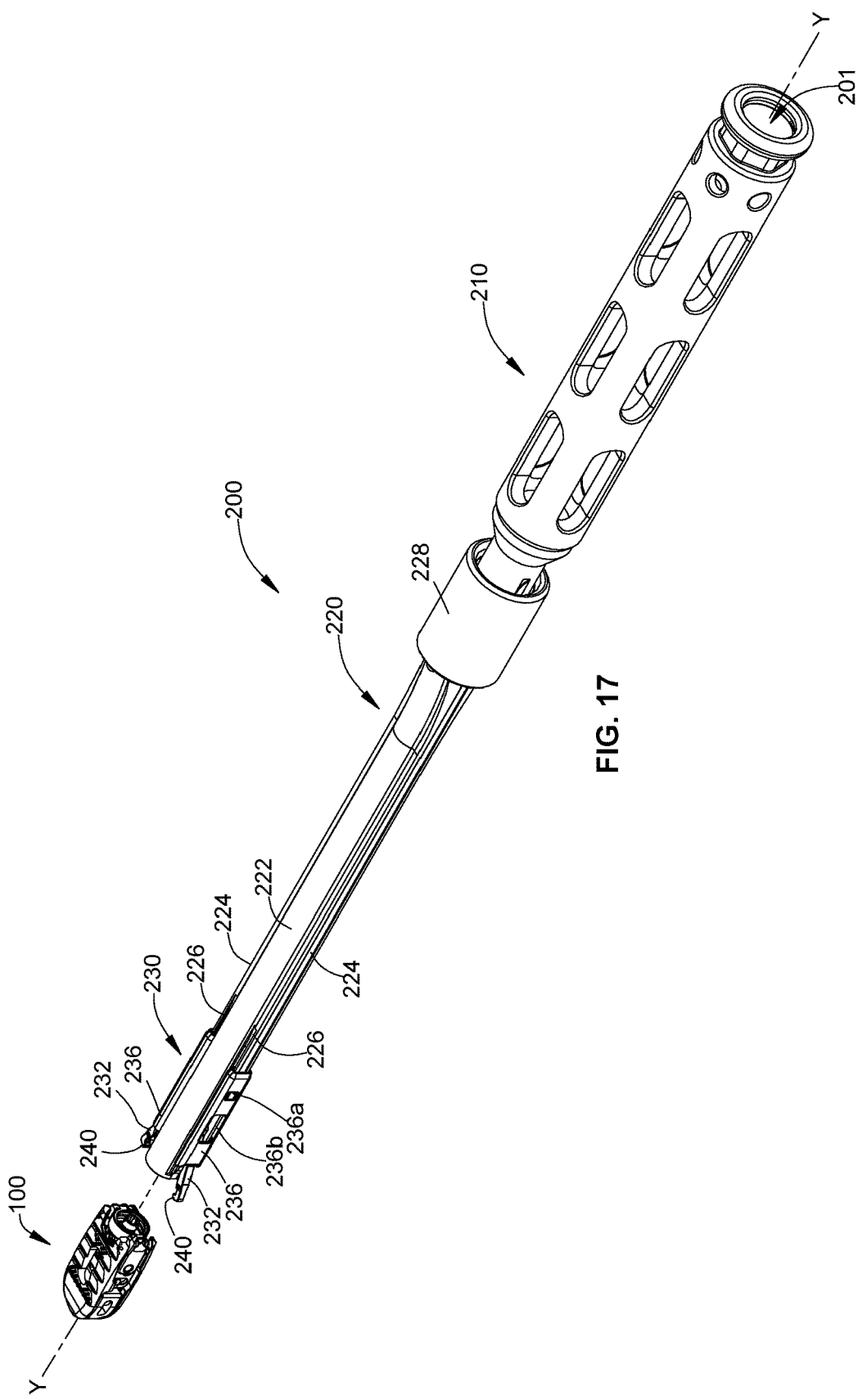
FIG. 17 is a perspective view of a system including the spinal implant of FIG. 1 and an insertion instrument, in accordance with an embodiment of the present disclosure.

Referring now to FIGS. 17-18B, the spinal implant 100 and an insertion instrument 200 are shown. The insertion instrument 200 includes, from proximal to distal, a handle 210, a body portion 220, and a connector assembly 230 extending along a longitudinal axis "Y" that is coincident with the longitudinal axis "X" (FIG. 1) of the spinal implant 100. A lumen 201 is defined through the insertion instrument 200 (i.e., the handle 210, the body portion 220, and the connector assembly 230) and configured to receive a tool 300 (see e.g., FIG. 22) such as, for example, driving instruments for rotating the threaded post 172 and/or the flange nut 154 of the spinal implant 100.

The body portion 220 includes an elongated shaft 222, elongated rails 224 slidably movable along tracks 226 disposed on opposed sides of the elongated shaft 222, and a rotation knob 228 disposed about a proximal portion 222a of the elongated shaft 222. The rotation knob 228 includes a threaded inner surface 228a that is threadably engaged with the proximal portion 222a of the elongated shaft 222, and a distal recess 228b defined in the inner surface 228a that is configured to receive proximal flanges 224a of the elongated rails 224.

Each of the elongated rails 224 includes a proximal flange 224a and a distal flange 224b. As discussed above, the proximal flanges 224a of the elongated rails 224 are engaged with the distal recess 228b of the rotation knob 228. The distal flanges 224b of the elongated rails 224 are engaged with respective proximal openings 236a defined in connector plates 236 of the connector assembly 230.

The connector assembly 230 includes connector arms 232 pivotally secured to opposed sides of the elongated shaft 222 of the body portion 220 via pivot pins 234, and connector plates 236 slidably disposed over the connector arms 232. Each of the connector arms 232 includes a proximal portion 232a and a distal portion 232b that are disposed at angles with respect to the longitudinal axis "Y" of the insertion instrument 200. The proximal portion 232a of each connector arm 232 includes a protrusion 238 on an outer surface thereof, and the distal portion 232b of each connector arm 232 includes an engagement feature 240 (e.g., a hook) on an inner surface thereof.

The connector plates 236 each include a u-shaped body configured to engage and longitudinally ride the tracks 226 of the elongated shaft 222. Each of the connector plates 236 includes a proximal opening 236a engaged with the respective distal flange 224b of the elongated rails 224, and a distal opening 236b configured to receive the respective protrusion 238 of the connector arms 232 when the connector arms 232 are disposed in a closed or grasping position.

As shown in FIGS. 19A and 19B, when the rotation knob 228 of the insertion instrument 200 is disposed in a proximal position, the elongated rails 224 and the connector plates 236 are also disposed in a proximal position. In the proximal position, the cover plates 236 are disposed over the proximal portions 232a of the connector arms 232 such that the proximal portions 232a are substantially aligned with the longitudinal axis "Y" of the insertion instrument 200, and the distal portions 232b of the connector arms 232 extend radially outwardly relative to the longitudinal axis "Y". In the proximal position, the connector arms 232 are in an open position such that the spinal implant 100 may be placed adjacent the connector assembly 230 of the insertion instrument 200, with the proximal cavities 158a of the linkage body 152 aligned with the engagement features 240 of the insertion instrument 200.

As shown in FIGS. 20A and 20B, the rotation knob 228 of the insertion instrument 200 may be moved to a distal position by rotating the rotation knob 228 in a first direction which causes a corresponding longitudinal movement of the elongated rails 224 and the connector plates 236 along the tracks 226 of the elongated shaft 222. The distal movement of the connector plates 236 over the connector arms 232 causes the connector arms 232 to pivot about the pivot pin 234 (FIG. 18B) such that the distal portions 232b of the connector arms 232 are substantially aligned/parallel with the longitudinal axis "Y" of the insertion instrument 200 and the proximal portions 232a of the connector arms 232 extend radially outwardly such that the protrusions 238 are deflected into the distal openings 236b of the connector plates 236. In the distal position, the connector arms 232 are in a closed or grasping position and the engagement features 240 of the insertion instrument 200 are engaged with the proximal cavities 158a of the spinal implant 100 thereby releasably securing the insertion instrument 200 to the spinal implant 100. As shown in FIGS. 19A-20B, the width of the body portion 220 of the insertion instrument 200, when attached to the spinal implant 100, is no wider than the spinal implant 100. This corresponding instrument body portion 220 width is important, as it facilitates insertion and manipulation of the spinal implant 100 with the insertion instrument 200 in the limited space available during surgery.

Figure 21:
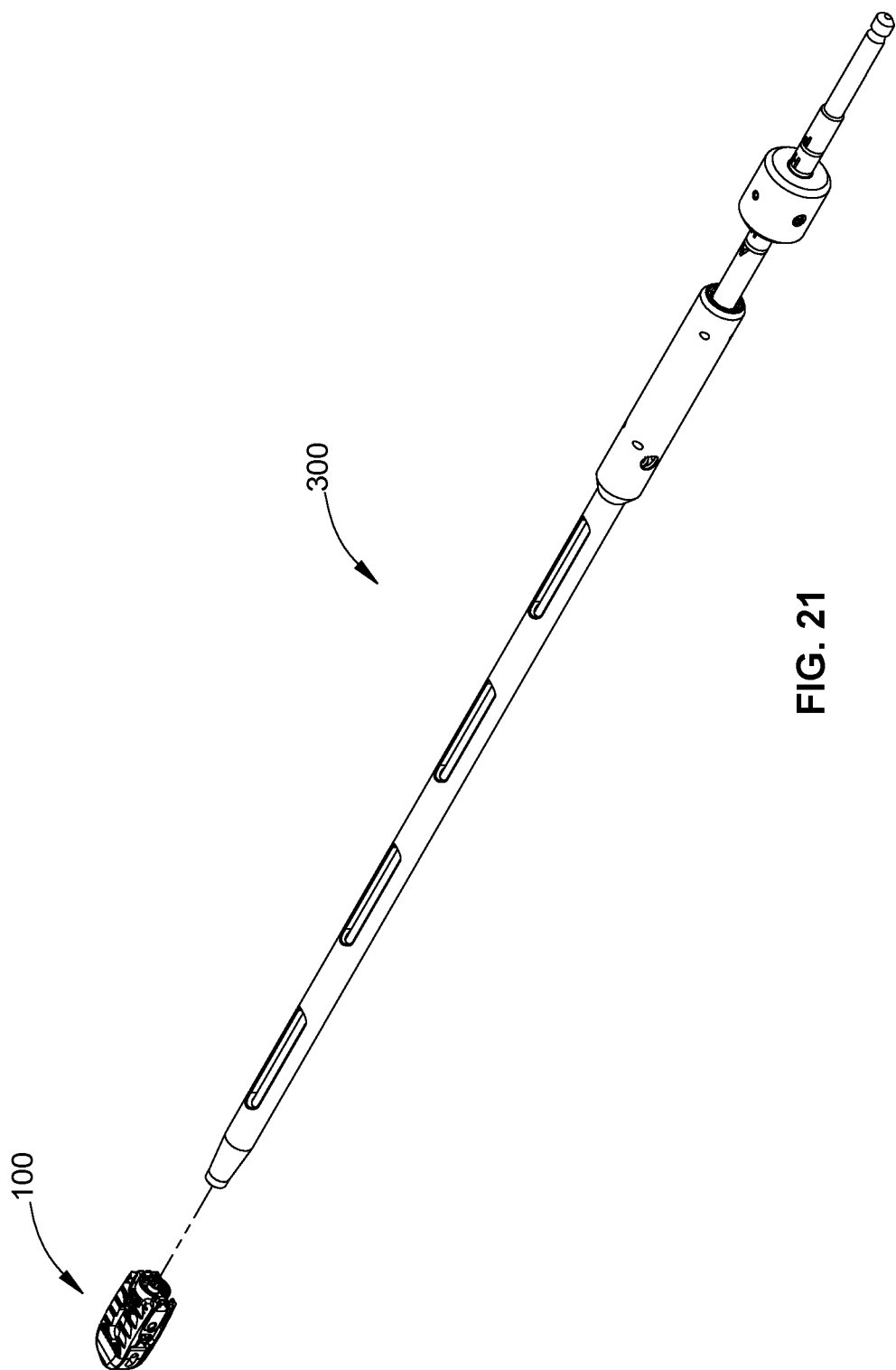
FIG. 21 is a perspective view of a system including the spinal implant of FIG. 1 and a driving instrument, in accordance with an embodiment of the present disclosure.
Figure 22:
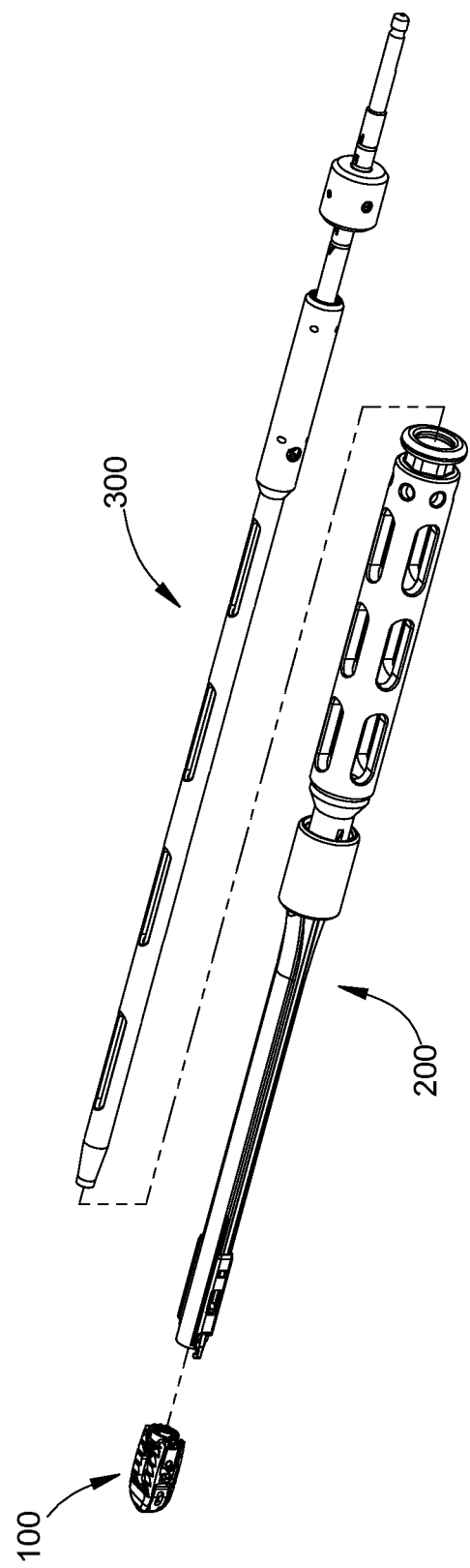
FIG. 22 is a perspective view of a system including the spinal implant of FIG. 1, the insertion instrument of FIG. 17, and the driving instrument of FIG. 21, in accordance with an embodiment of the present disclosure.

Additionally or alternatively, as shown in FIGS. 21 and 22, a driving instrument 300 may be used with the spinal implant 100, alone (FIG. 21) or in conjunction with the insertion instrument 200 (FIG. 22).

Figure 23:
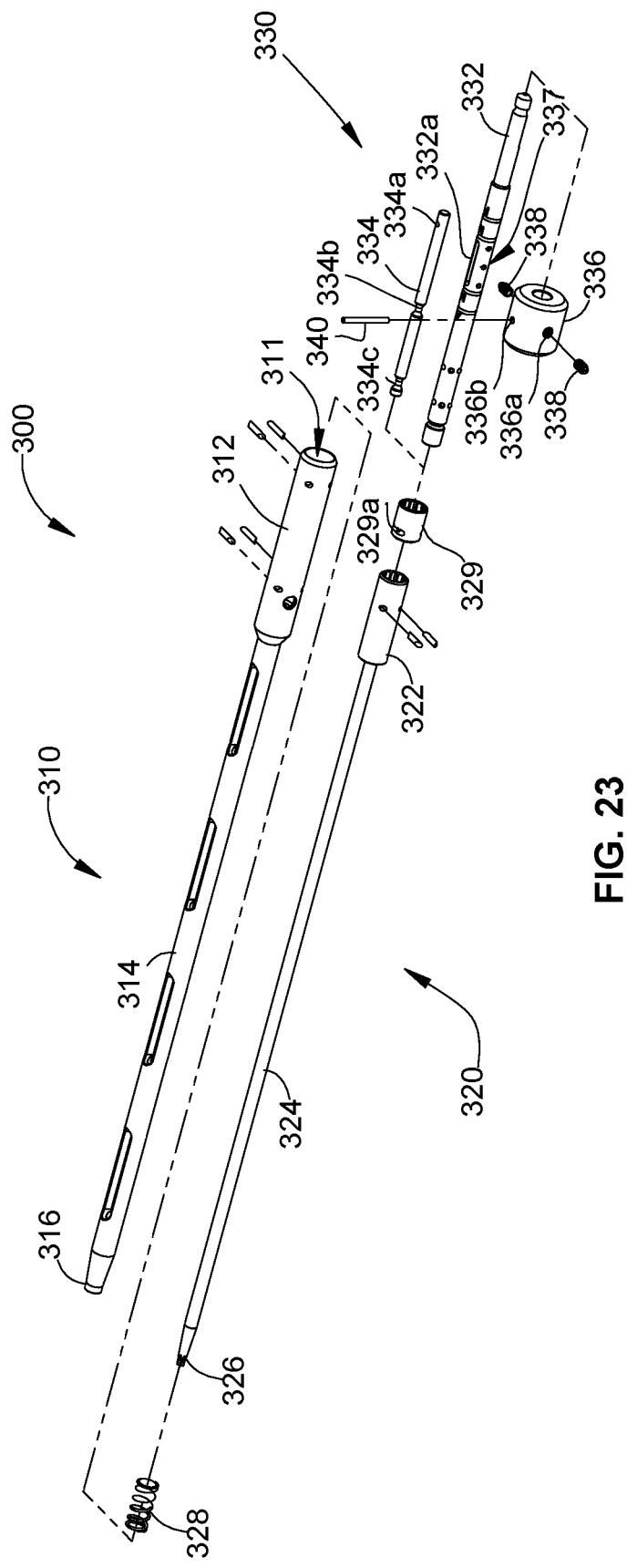
FIG. 23 is a perspective view of the driving instrument of FIGS. 21 and 22, with parts separated.

With reference now to FIG. 23, the driving instrument 300 includes an outer shaft 310, a distal inner shaft 320, and a proximal shaft assembly 330. The outer shaft 310 defines a lumen 311 therethrough, and includes a proximal base portion 312 and an elongated body portion 314 terminating at an open tip 316. The open tip 316 includes an inner surface 316a (see e.g., FIG. 24B) that is complementary in shape with the shaped outer surface 165 (see e.g., FIG. 2) of the flange nut 154 of the spinal implant 100 to engage the flange nut 154.

The distal inner shaft 320 includes a proximal base portion 322 and an elongated body portion 324 terminating at a distal tip 326. The proximal base portion 322 is disposed within the proximal base portion 312 of the outer shaft 310, and the elongated body 324 is disposed within the elongated body portion 314 of the outer shaft 310. The distal inner shaft 320 is biased in a proximal position via a biasing member 328 (e.g., a coiled spring) disposed over the elongated body 324 and within the proximal base portion 312 of the outer shaft 310. A connector 329 is also disposed within the proximal base portion 312 of the outer shaft 310, proximal to the proximal base portion 322 of the distal inner shaft 320. The distal tip 326 is a male connector having a complementary geometry to the recessed proximal end 172b (see e.g., FIG. 2) of the threaded post 172 (e.g., a hex feature) such that the distal tip 326 is receivable therein and configured to engage the threaded post 172.

Figure 26A:
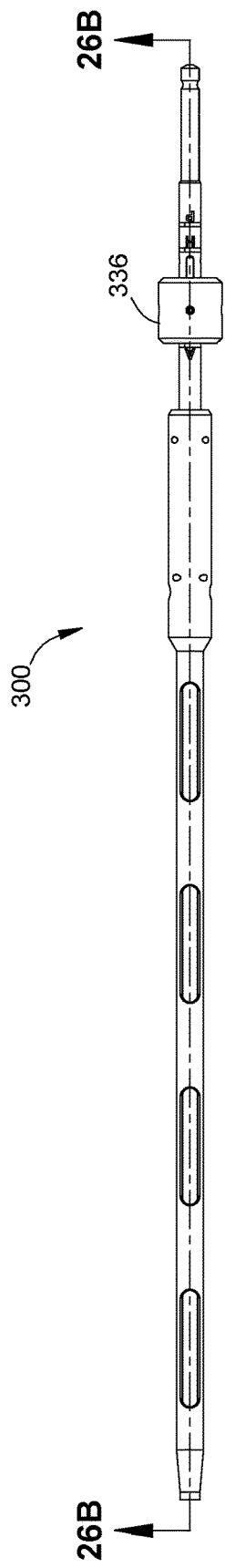
FIG. 26A is a side view of the driving instrument of FIGS. 21 and 22, in an anterior position.
Figure 26B:
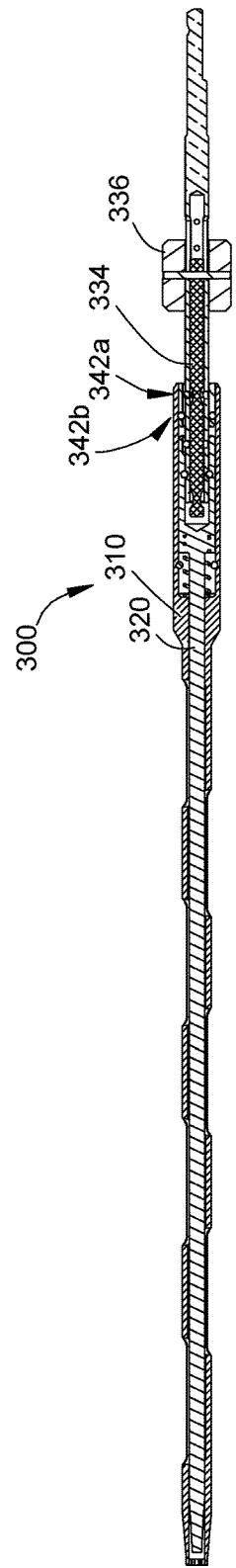
FIG. 26B is a cross-sectional view of the driving instrument of FIG. 26A, taken along line 26B-26B of FIG. 26A.

The proximal shaft assembly 330 includes a proximal outer shaft 332, a proximal inner shaft 334, and an adjustment knob 336. The proximal outer shaft 332 is configured to be slidably disposed within the connector 329 and the proximal base portion 322 of the distal inner shaft 320, which are each disposed within the outer shaft 310, as described above. The adjustment knob 336 is slidably disposed over the proximal outer shaft 332 and the proximal inner shaft 334 is disposed within the proximal outer shaft 332. Threaded plungers 338 are positioned in lateral side openings 336a of the adjustment knob 336 and are configured to engage recesses 337 defined in the proximal outer shaft 332 upon actuation of the adjustment knob 336 between a height position "H" (FIGS. 24A and 24B), a posterior or proximal position "P" (FIGS. 25A and 25B), and an anterior or distal position "A" (FIGS. 26A and 26B). A pin 340 extends through opposed openings 336b of the adjustment knob 336, a longitudinal opening 332a defined in the proximal outer shaft 332, and an opening 334a defined through the proximal inner shaft 334. Accordingly, the adjustment knob 336 may be slid between the height position "H" (FIGS. 24A and 24B), the proximal position "P" (FIGS. 25A and 25B), and the distal position "A" (FIGS. 26A and 26B) relative to the proximal outer shaft 332 which, in turn, causes a corresponding longitudinal movement of the proximal inner shaft 334.

The proximal inner shaft 334 further includes proximal and distal recessed grooves 334b, 334c defined therearound, and the connector 329 includes pockets 329a defined therethrough. The proximal and distal recessed grooves 334b, 334c as well as the pockets 329 are configured to engage/disengage proximal and/or distal ball bearing assemblies 342a, 342b (see e.g., FIG. 24B) disposed within the proximal outer shaft 332 during actuation of the adjustment knob 336 between the height, proximal, and distal positions to effect the function of the driving instrument 300. Specifically, the proximal and distal ball bearing assemblies 324a, 342b are configured to float above or below the proximal outer shaft 332 to actively engage or disengage the distal inner shaft 320 and/or the outer shaft 310.

Figure 24A:
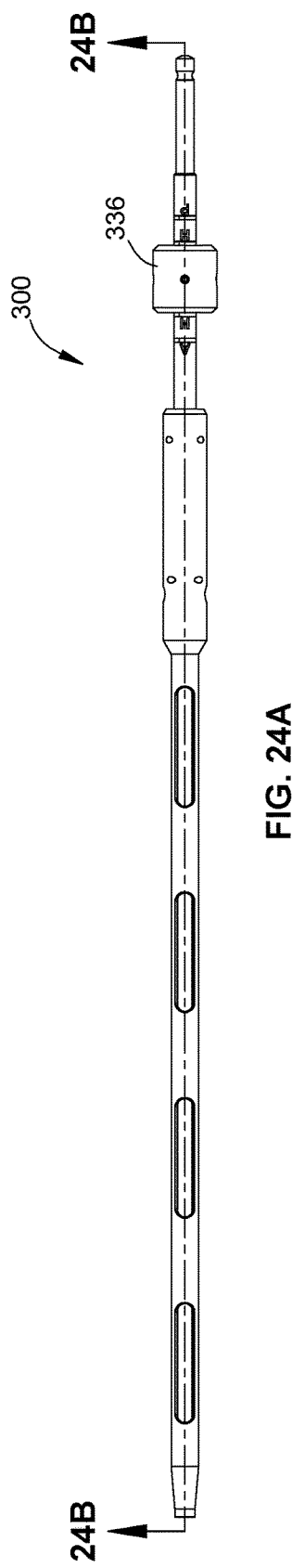
FIG. 24A is a side view of the driving instrument of FIGS. 21 and 22, in a height position.
Figure 24B:
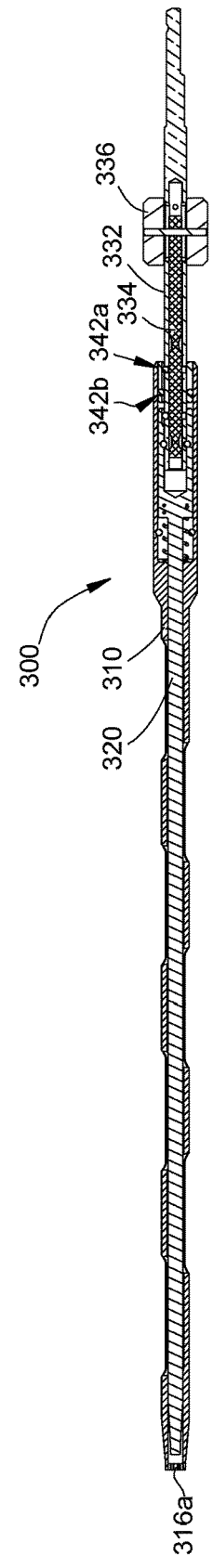
FIG. 24B is a cross-sectional view of the driving instrument of FIG. 24A, taken along line 24B-24B of FIG. 24A.

As shown in FIGS. 24A and 24B, when the adjustment knob 336 is in the height position "H", the proximal and distal ball bearing assemblies 342a, 342b are disengaged from the proximal and distal recessed grooves 334b, 334c (FIG. 23) of the proximal inner shaft 334, as well as the pockets 329a (FIG. 23) of the connector 329. Accordingly, actuation of the proximal outer shaft 332 of the proximal adjustment assembly 330 allows both the outer shaft 310 and the distal inner shaft 320 to be actuated such that the proximal and distal adjustment assemblies 150, 170 of the spinal implant 100 are simultaneously adjusted.

When the adjustment knob 336 is moved to the posterior position "P", as shown in FIGS. 25A and 25B, the proximal inner shaft 334 is slid proximally such that the proximal ball bearing assembly 342a is disengaged from the proximal inner shaft 334 and the distal ball bearing assembly 342b is engaged with the pocket 329a of the connector 329. Accordingly, actuation of the proximal outer shaft 332 of the proximal adjustment assembly 330 causes only the outer shaft 310 to be actuated such that only the proximal region 110a of the spinal implant 100 is actuated.

When the adjustment knob 336 is moved to the anterior position "A", as shown in FIGS. 26A and 26B, the proximal inner shaft 334 is slid distally such that the proximal ball bear assembly 342a is engaged with the proximal recessed groove 334c of the proximal inner shaft 334 and the distal ball bearing assembly 342b is disengaged from the pockets 329a of the connector 329. Accordingly, actuation of the proximal outer shaft 332 of the proximal adjustment assembly 330 causes only the distal inner shaft 320 to be actuated such that only the distal region 110b of the spinal implant 100 is actuated.

It is envisioned that a feedback mechanism (e.g., audible, tactile, etc.) may be incorporated into the insertion instrument 200 and/or the driving instrument 300 to provide an indication to the clinician of expansion and/or retraction of the proximal and/or distal adjustment assemblies 150, 170 of the spinal implant 100. For example, the insertion instrument 200 and/or the driving instrument 300 may include a ratchet such that each turn, or portion of a turn, produces an audible sound (e.g., a click) to alert the clinician that the spinal implant 100 is being expanded and/or retracted. Further, each audible click may represent expansion or contraction of a predetermined amount (e.g., 2 mm). Additionally or alternatively, the insertion instrument 200 and/or the driving instrument 300 may include a quick release feature (e.g., that releases a ratchet) so that the surgical implant 100 can be quickly reduced.

Figure 27:
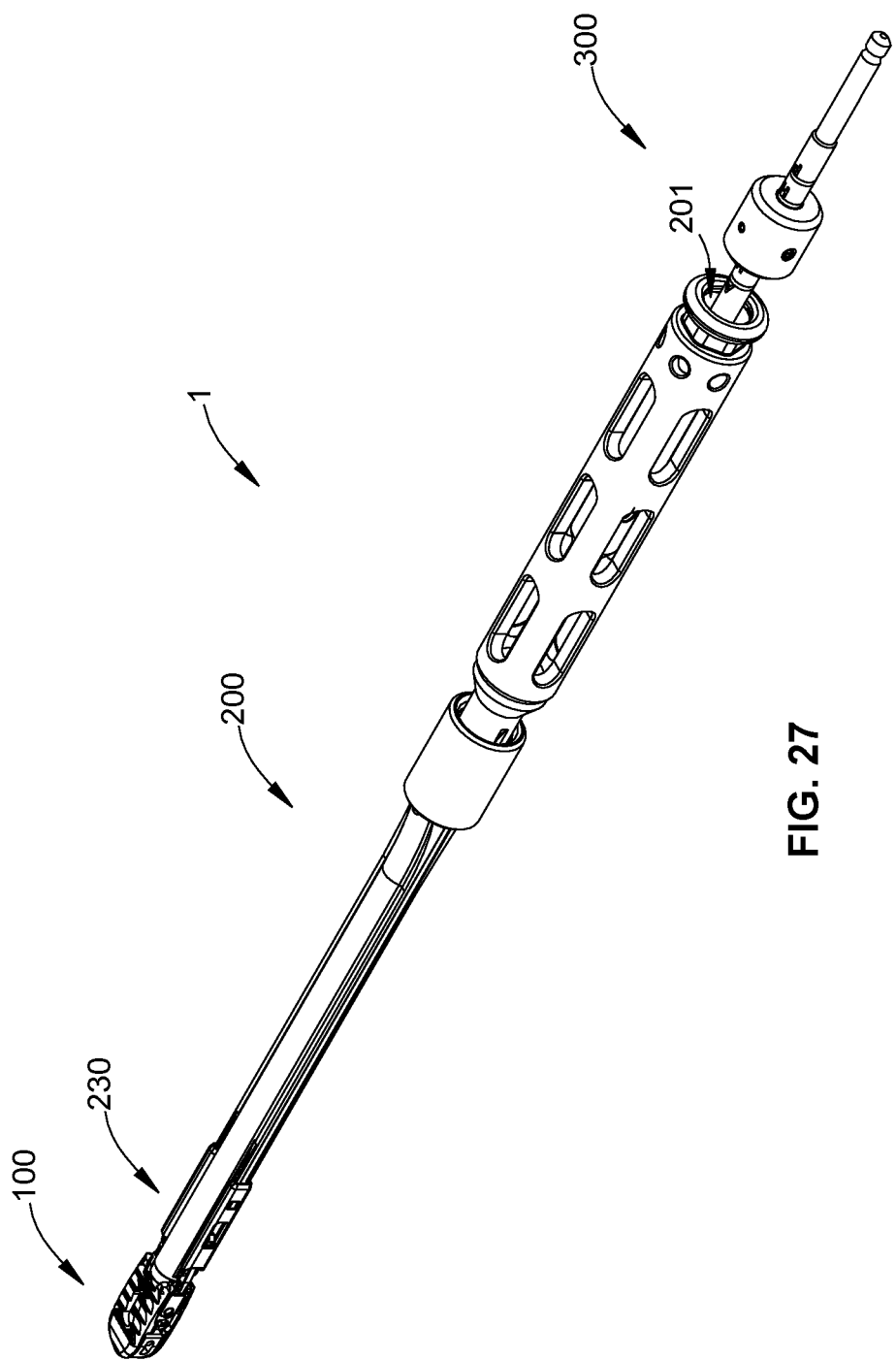
FIG. 27 is a perspective view of the system of FIG. 22.

Referring now to FIG. 27, a system 1 for inserting, positioning, and/or adjusting (e.g., expanding) the spinal implant 100 in a disc space between adjacent vertebral bodies with the insertion instrument 200 and the driving instrument 300 is shown. A clinician removes all or a portion of a disc from between two vertebral bodies (e.g., complete or partial diskectomy), and scrapes and cleans the endplates of the vertebral bodies to prepare the surfaces for placement of the spinal implant 100 such that a fusion will occur. Next, the clinician places the spinal implant 100 into the disc space using the insertion instrument 200 by aligning and releasably securing the connector assembly 230 of the insertion instrument 200 to the spinal implant 100, as described above. The insertion instrument 200 may be pre-attached to the spinal implant 100 prior to inserting the spinal implant 100 into the disc space, or may be attached after the spinal implant 100 is positioned in the disc space. A slap hammer (not shown) may be used with or integrated into the insertion instrument 200 to facilitate placement of the spinal implant 100 into the disc space.

Figure 28C:
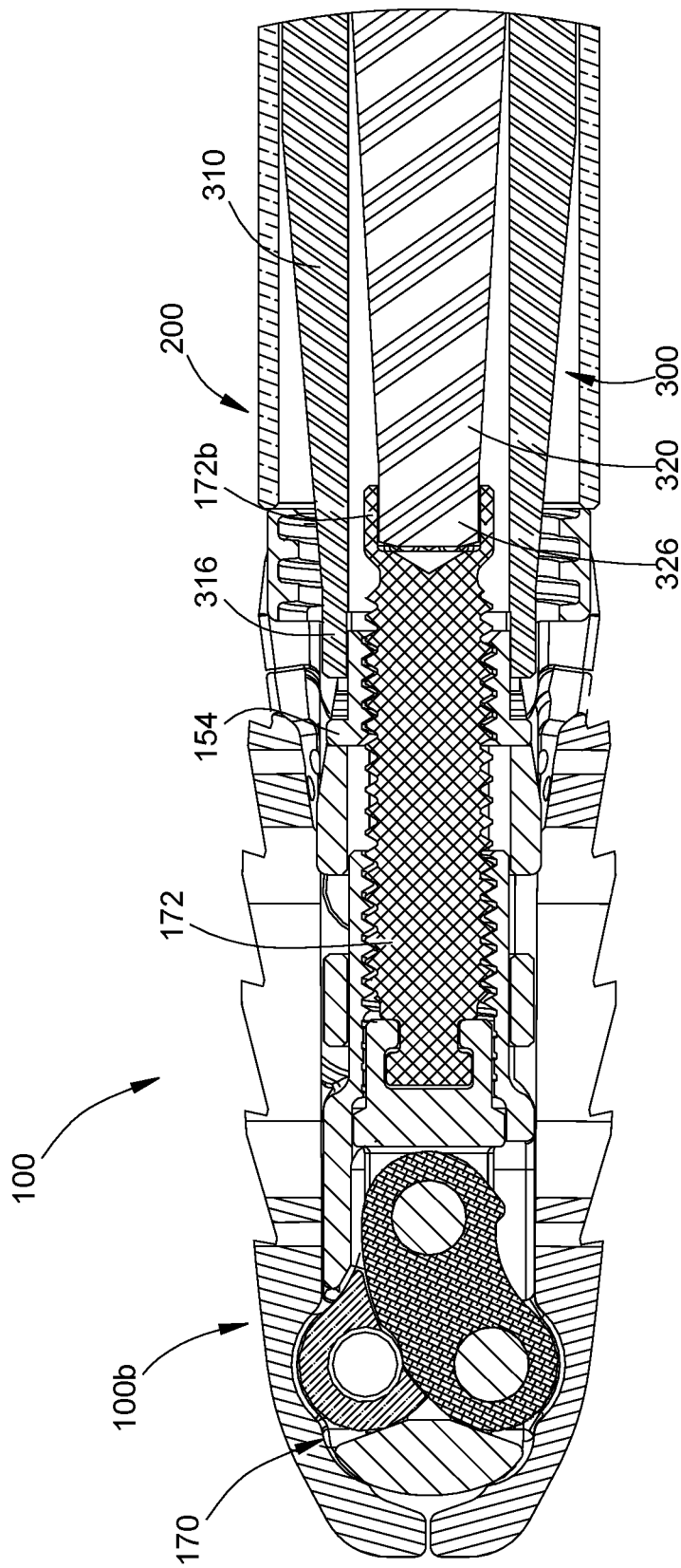
FIG. 28C is a close-up view of the area of detail indicated in FIG. 28B.

The driving instrument 300, which is positioned in the home position "H", is then inserted through the lumen 201 of the insertion instrument 200. As shown in FIGS. 28A-28C, the driving instrument 300 extends through the insertion instrument 200 such that the open tip 316 of the outer shaft 310 engages the flange nut 154 of the spinal implant 100 and the distal tip 326 of the distal inner shaft 320 engages the recessed proximal end 172b of the threaded post 172. The clinician may then moves the adjustment knob 336 of the driving instrument 300 to the anterior position "A", as described above, to actively engage the distal inner shaft 320 (and disengage the outer shaft 310) such that rotation of the proximal outer shaft 332 in a first or second direction rotates the threaded post 172 which, in turn, actuates the distal adjustment assembly 170 of the spinal implant 100, as described above, to adjust the position (i.e., height) of the distal region 100b of the spinal implant 100.

Figure 29C:
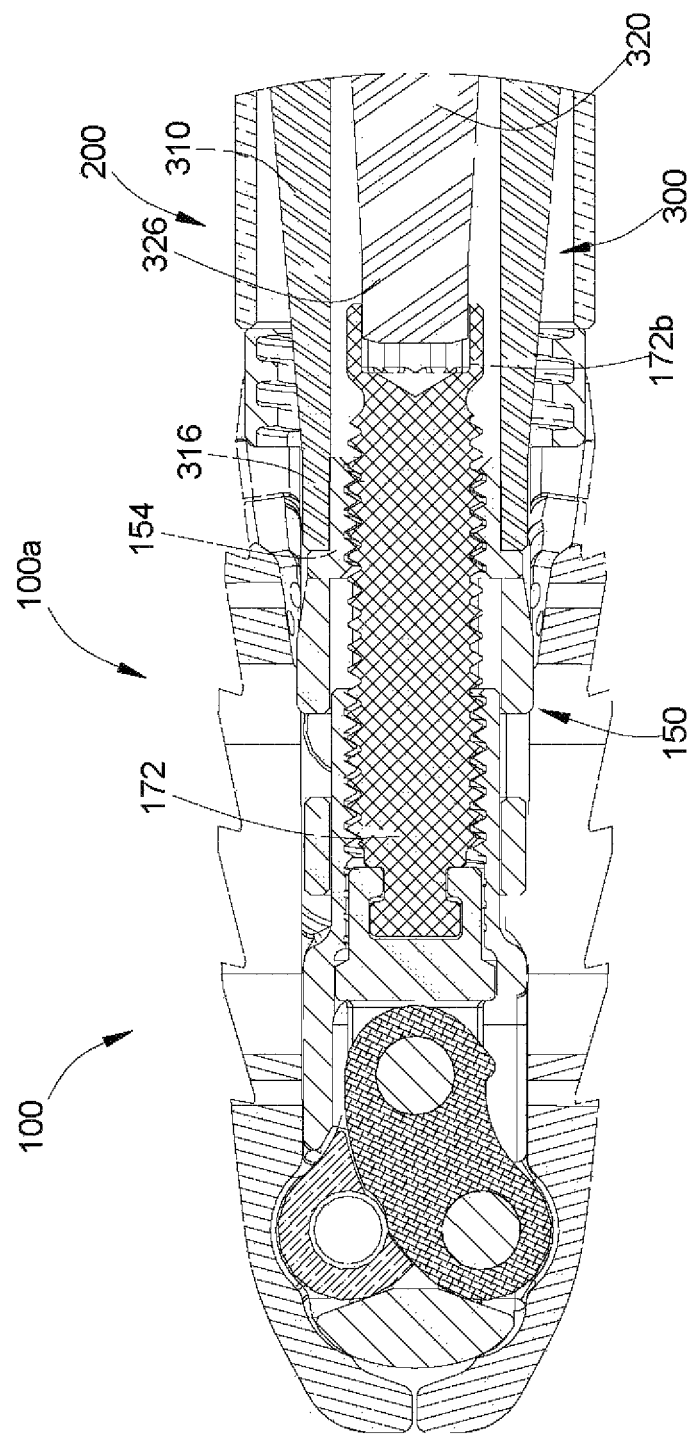
FIG. 29C is a close-up view of the area of detail indicated in FIG. 29B.

Additionally or alternatively, the clinician can move the adjustment knob 336 of the driving instrument 300 to the posterior position "P", as shown in FIGS. 29A-29C and described above, to actively engage the outer shaft 310 (and disengage the distal inner shaft 320) such that rotation of the proximal outer shaft 332 in a first or section direction rotates the flange nut 154 of the spinal implant 100 which, in turn, actuates the proximal adjustment assembly 150 of the spinal implant 100, as described above, to adjust the position (i.e., height) of the proximal region 100a of the spinal implant 100.

Various allograft and/or autograft materials may be placed into and/or next to the spinal implant 100 to assist in the fusion process. By way of example, it is contemplated that a catheter or similar tubular instrument may be inserted through the lumen 201 of the insertion instrument 200 after the driving instrument 300 is removed. Bone or other natural or synthetic graft material may then be injected through the catheter or tubular instrument to exit at the far end of the instrument to provide graft material in and around the spinal implant 100. Should the clinician need to adjust the proximal and/or distal heights of the spinal implant 100 once it is expanded, the driving instrument 300 would be re-engaged with the flange nut 154 and/or the threaded post 172, the adjustment knob 336 would be moved to the posterior or anterior position, and the proximal outer shaft 332 would be rotated to drive the flange nut 154 or the threaded post 172 proximally or distally.

While embodiments shown and described herein illustrate exemplary heights of the spinal implant in collapsed, partially expanded, and fully expanded positions, it should be understood that other unexpanded and expanded heights are also contemplated. Thus, it is contemplated that a variety of inserting and expanding techniques are achievable with the spinal implant, the insertion instrument, and driving instrument disclosed herein.

For example, the spinal implant attached to the insertion instrument may be inserted into a disc space between vertebrae with the end plates of the exterior surfaces of the upper and lower bodies of the spinal implant substantially parallel. The driving instrument may then be used to actuate the proximal and distal adjustment assemblies such that the spinal implant is expanded while maintaining the upper and lower bodies substantially parallel to one another until the vertebral bodies are engaged. Thereafter, the proximal and distal adjustment assemblies may be individually actuated to adjust the disposition of the upper and lower bodies to accommodate lordosis. Alternatively, after the spinal implant is inserted into a disc space with the upper and lower bodies substantially parallel, one of the proximal or distal regions of the spinal implant may be expanded by actuating the corresponding proximal or distal adjustment assembly, followed by either (i) expanding the proximal and distal regions of the spinal implant simultaneously to provide further parallel expansion, or (ii) expanding the other of the proximal or distal adjustment assembly to adjust the other region of the spinal implant into contact with the vertebral bodies. Thereafter, the spinal implant may be (i) locked in place with the set screw as described below, (ii) further expanded or retracted in parallel by actuating the proximal and distal adjustment assemblies at the same time, or (iii) further adjusted to conform to the anatomy by alternately actuating one or both of the proximal and distal adjustment assemblies.

It is further contemplated that the spinal implant may be adjusted to approximate the lordosis of the patient by adjusting one or both of the proximal and distal adjustment assemblies prior to inserting the spinal implant into the disc space, thereby approximating the pre-existing lordotic condition of the patient. After the spinal implant is so adjusted and inserted, the driving instrument may then be used to actuate the proximal and distal adjustment assemblies such that the spinal implant is expanded until the vertebral bodies are engaged. Thereafter, the proximal or distal adjustment assembly may be actuated to adjust the disposition of the upper and lower bodies of the spinal implant to accommodate lordosis. Alternatively, after the spinal implant is inserted with the upper and lower bodies predisposed for lordosis, one of the proximal or distal regions of the spinal implant may be expanded by actuating the corresponding proximal or distal adjustment assembly, followed by either (i) expanding the proximal and distal regions of the spinal implant simultaneously, or (ii) expanding the other of the proximal or distal adjustment assembly to adjust the other region of the spinal implant into contact with the vertebral bodies. Thereafter, the spinal implant may be (i) locked in place with the set screw as described below, (ii) further expanded or retracted in parallel by actuating the proximal and distal adjustment assemblies at the same time, or (iii) further adjusted to conform to the anatomy by alternately actuating one or both of the proximal and distal adjustment assemblies.

Figure 30:
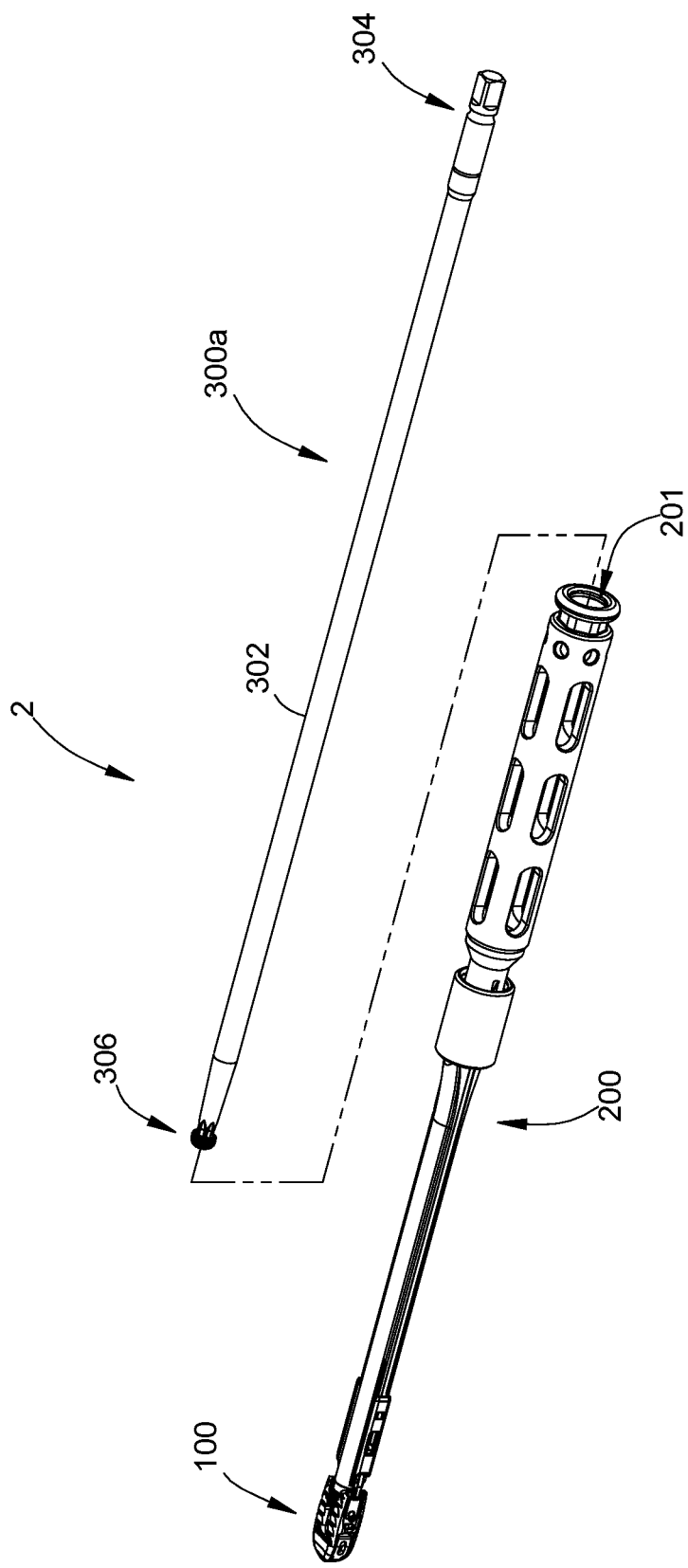
FIG. 30 is a perspective view of a system including the spinal implant of FIG. 1, the insertion instrument of FIG. 17, and a set screw driver in accordance with another embodiment of the present disclosure.

After the spinal implant 100 is manipulated into a desired position, a set screw driver 300a may be utilized to lock the set screw 10 into the spinal implant 100 to prevent backout of the threaded post 172 and flange nut 154. As shown in FIG. 30, a system 2 includes the spinal implant 100, the insertion instrument 200, and a set screw driver 300a. The set screw driver 300a includes an elongated body 302 having a proximal end 304 configured to engage a rotation instrument (not shown, but which may constitute a T-handle) and a distal end 306 configured to engage the set screw 10 (see e.g., FIG. 1). The set screw driver 300a, having the set screw 10 releasable attached thereto, is introduced through the lumen 201 of the insertion instrument 200 such that the set screw 10 may be screwed into the threaded inner surface 153 of the linkage body 152 to lock the spinal implant 100 in the desired position.

Figure 31:
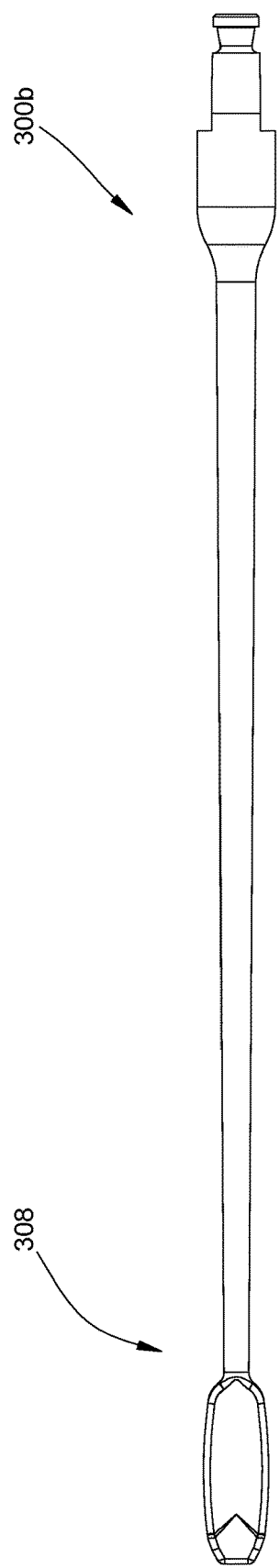
FIG. 31 is a top view of a disc spreader in accordance with an embodiment of the present disclosure.
Figure 32:
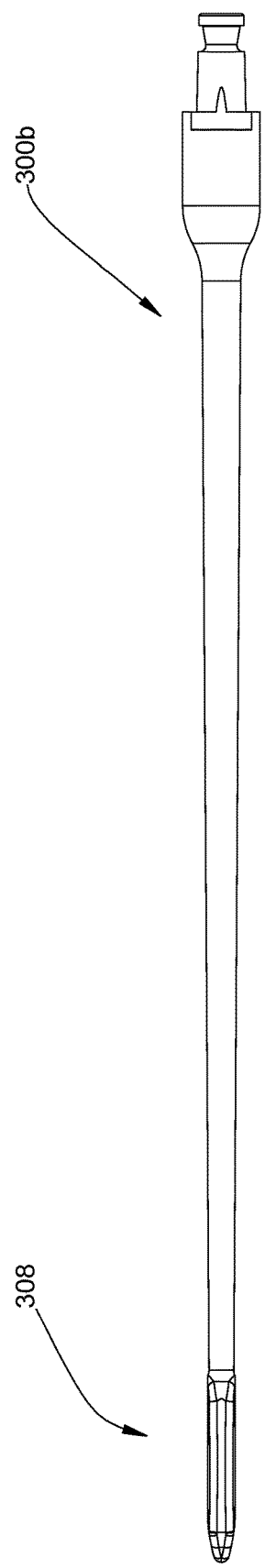
FIG. 32 is a side view of the disc spreader of FIG. 31.
Figure 33:
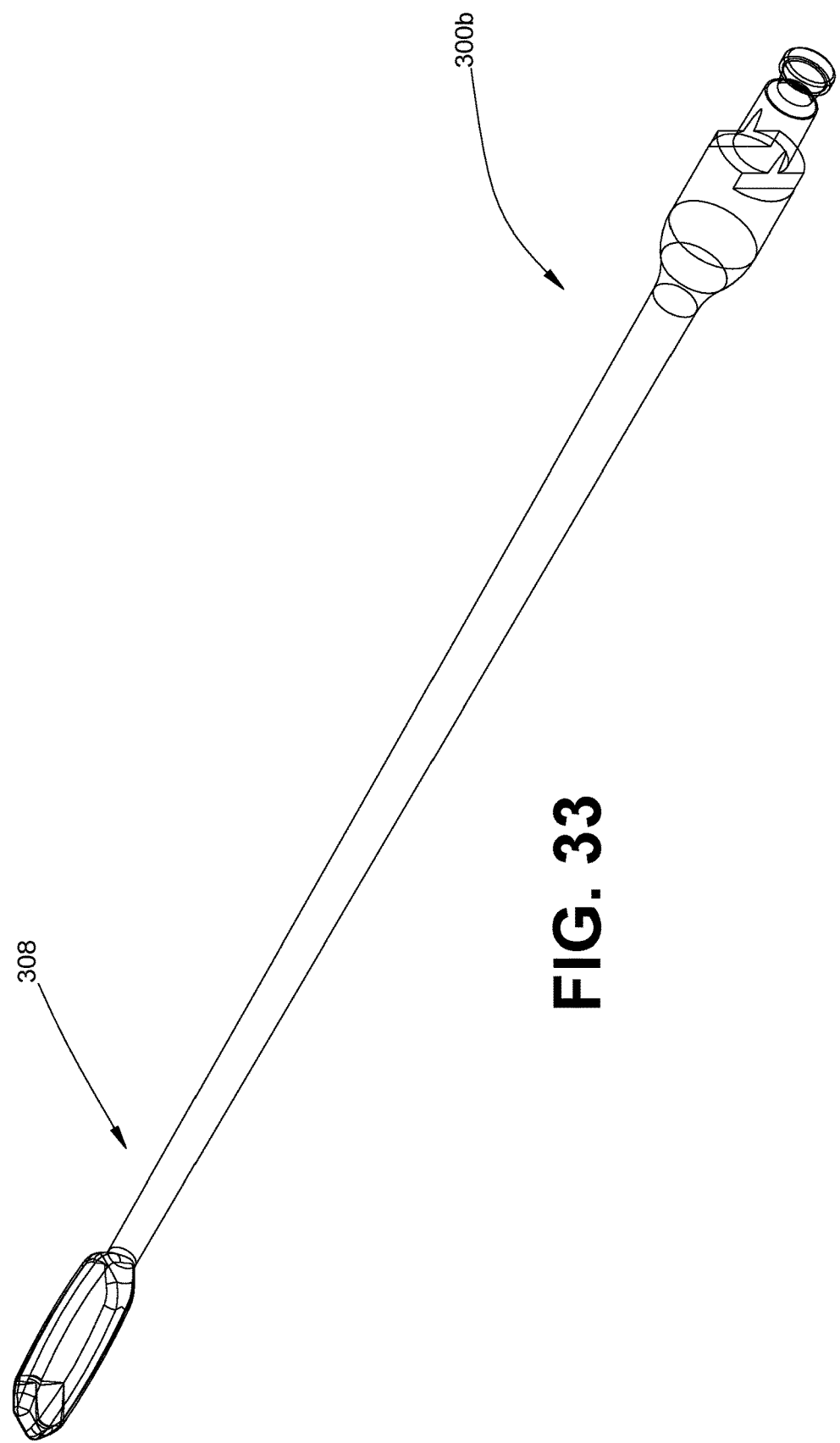
FIG. 33 is a perspective view of the disc spreader of FIGS. 31 and 32.

With reference now to FIGS. 31-33, prior to the insertion of the spinal implant 100 into a disc space, a disc spreader 300b having a blade portion 308 at a distal end thereof may be utilized to distract the disc space. The blade portion 308 may be sized to act as a trial implant prior to deploying a spinal implant 100 into the disc space. In embodiments, the blade portion 308 is releasably secured to the distal end of the disc spreader 300b such that a variety of trial implants may be attached thereto. The size of the trial implants may range, for example, in 1 to 2 mm increments and may include both lordotic and parallel versions.

A spinal fixation system may be provided in a kit. The kit is an assembled package including at least one spinal implant 100, an insertion instrument 200, a driving instrument 300, a set screw driver 300a, and a disc spreader 300b including a plurality of blade portions 308. In embodiments, the kit may include a plurality of spinal implant 100 having, for example, different expansion sizes.

Persons skilled in the art will understand that the structures and methods specifically described herein and shown in the accompanying figures are non-limiting exemplary embodiments, and that the description, disclosure, and figures should be construed merely as exemplary of particular embodiments. By way of example, it is contemplated that the insertion instrument and/or driving instrument may be provided with indicia or other markings or references to indicate the relative position of the threaded post and/or flange nut, so that the position of the upper and lower bodies relative to one another can be understood from the positon of the instrument handles. It is further contemplated that the threaded inner surface of the linkage body provided for the set screw may be used to engage an instrument to hold the spinal implant, either during insertion or removal. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A spinal implant having a proximal region and a distal region, the spinal implant comprising:
   an upper body including an outer surface and an inner surface;
   a lower body including an outer surface and an inner surface, the inner surfaces of the upper and lower bodies disposed in opposed relation relative to each other;
   a proximal adjustment assembly disposed between the upper and lower bodies in the proximal region of the spinal implant and adjustably coupled to the upper and lower bodies;
   a distal adjustment assembly disposed between the upper and lower bodies in the distal region of the spinal implant and adjustably coupled to the upper and lower bodies, wherein the proximal and distal adjustment assemblies are independently movable, both concurrently and alternately, to change a vertical height of at least one of the proximal region or the distal region of the spinal implant; and
   a set screw removably disposed within the proximal region of the spinal implant to lock the vertical height of the proximal and distal regions of the spinal implant.

2. The spinal implant according to claim 1, wherein the distal adjustment assembly includes a pivot linkage assembly including an upper pivot linkage pivotably connected to the inner surface of the upper body, a lower pivot linkage pivotably connected to the inner surface of the lower body, and a connector linkage pivotably connected to the upper and lower pivot linkages such that longitudinal movement of the connector linkage causes a corresponding movement of the upper and lower pivot linkages with respect to each other to change the vertical height of the distal region of the spinal implant.

3. The spinal implant according to claim 2, wherein the distal adjustment assembly includes a threaded post including an elongated threaded body extending through the proximal adjustment assembly and a distal end disposed within a recess defined in the connector linkage such that longitudinal translation of the threaded post effects movement of the pivot linkage assembly.

4. The spinal implant according to claim 3, wherein the distal adjustment assembly includes an expander including a body portion defining a cavity therein and a distal end including a double ramped inner surface, wherein the pivot linkage assembly extends through the cavity of the expander such that the upper and lower pivot linkages contact the double ramped inner surface of the expander when moved by the threaded post.

5. The spinal implant according to claim 4, wherein the expander includes a shaft extending proximally from the body portion, the shaft including a threaded opening defined therein, and wherein the elongated threaded body of the threaded post is threadably engaged with the threaded opening of the shaft and axially movable therethrough into the cavity of the expander.

6. The spinal implant according to claim 3, wherein each of the inner surfaces of the upper and lower bodies includes a pair of proximal fins defining angled slots therethrough, and wherein the proximal adjustment assembly includes:
   a linkage body including distal holes defined through lateral sides thereof; and
   a first set of pins disposed within the distal holes of the linkage body and into the angled slots of the upper and lower bodies,
   such that movement of the linkage body causes the first set of pins to translate within the angled slots to change the vertical height of the proximal region of the spinal implant.

7. The spinal implant according to claim 6, wherein the proximal adjustment assembly includes a flange nut having a threaded opening defined therethrough that is threadably engaged with the threaded post of the distal adjustment assembly, and the linkage body includes a recess disposed between proximal and distal portions thereof in which the flange nut is disposed, and wherein axial movement of the flange nut along the threaded post effects movement of the linkage body.

8. The spinal implant according to claim 7, wherein the proximal portion of the linkage body includes a threaded inner surface, and the set screw includes a threaded outer surface threadably engageable with the threaded inner surface of the linkage body to prevent the threaded post and the flange nut from moving proximally with respect to the linkage body.

9. The spinal implant according to claim 6, wherein the pair of proximal fins of the upper and lower bodies defines vertical slots therethrough, and wherein the proximal adjustment assembly includes a coupler that includes a pair of nubs extending from lateral sides thereof that is slidably disposed within the vertical slots of the upper and lower bodies.

10. The spinal implant according to claim 1, wherein at least one of the outer surfaces of the upper body or the lower body includes a plurality of tapered ridges.

11. A system comprising:
a spinal implant having a proximal region and a distal region, the spinal implant comprising:
an upper body including an outer surface and an inner surface;
a lower body including an outer surface and an inner surface, the inner surfaces of the upper and lower bodies disposed in opposed relation relative to each other;
a proximal adjustment assembly disposed between the upper and lower bodies in the proximal region of the spinal implant and adjustably coupled to the upper and lower bodies; and
a distal adjustment assembly disposed between the upper and lower bodies in the distal region of the spinal implant and adjustably coupled to the upper and lower bodies, wherein the proximal and distal adjustment assemblies are independently movable, both concurrently and alternately, to change a vertical height of at least one of the proximal region or the distal region of the spinal implant; and
an insertion instrument comprising:
a body portion including an elongated shaft extending along a longitudinal axis; and
a connector assembly including connector arms pivotably secured to opposed sides of the elongated shaft, the connector arms configured to engage an outer surface of the spinal implant.

12. The system according to claim 11, wherein the proximal adjustment assembly of the spinal implant includes a linkage body pivotably coupled to the upper and lower bodies, the linkage body including proximal cavities defined in lateral sides thereof, and each connector arm of the insertion instrument includes an engagement feature radially movable relative to the longitudinal axis such that the engagement features are movable in and out of engagement with the proximal cavities of the spinal implant.

13. The system according to claim 12, wherein each engagement feature is disposed on a distal portion of the respective connector arm and the connector assembly includes connector plates slidably disposed over the connector arms such that when the connector plates are disposed in a proximal position, the distal portions of the connector arms extend radially outwardly relative to the longitudinal axis and when the connector plates are disposed in a distal position, the distal portions of the connector arms are substantially aligned with the longitudinal axis.

14. The system according to claim 13, wherein the body portion of the insertion instrument includes elongated rails slidably disposed on the opposed sides of the elongated shaft, the elongated rails coupled to the connector plates of the connector assembly such that longitudinal movement of the elongated rails causes a corresponding longitudinal movement of the connector plates between the proximal and distal positions.

15. The system according to claim 14, wherein the body portion of the insertion instrument includes a rotation knob threadably engaged with a proximal portion of the elongated shaft and coupled to proximal ends of the elongated rails such that rotation of the rotation knob causes longitudinal movement of the elongated rails.

16. The system according to claim 11, further including a driving instrument positionable through a lumen defined through the insertion instrument, the driving instrument configured to actuate the proximal and distal adjustment assemblies.

17. The system according to claim 11, further including a set screw driver positionable through a lumen defined through the insertion instrument, the set screw driver configured to engage a set screw with the spinal implant to lock a position of the spinal implant.

18. A system comprising:
a spinal implant having a proximal region and a distal region, the spinal implant comprising:
an upper body including an outer surface and an inner surface;
a lower body including an outer surface and an inner surface, the inner surfaces of the upper and lower bodies disposed in opposed relation relative to each other;
a proximal adjustment assembly disposed between the upper and lower bodies in the proximal region of the spinal implant and adjustably coupled to the upper and lower bodies; and
a distal adjustment assembly disposed between the upper and lower bodies in the distal region of the spinal implant and adjustably coupled to the upper and lower bodies, wherein the proximal and distal adjustment assemblies are independently movable, both concurrently and alternately, to change a vertical height of at least one of the proximal region or the distal region of the spinal implant; and
a driving instrument including:
an outer shaft including a distal end configured to actuate the proximal adjustment assembly;
a distal inner shaft disposed within the outer shaft and including a distal end configured to actuate the distal adjustment assembly; and
a proximal shaft assembly including a proximal outer shaft, a proximal inner shaft disposed within the proximal outer shaft, and an adjustment knob for adjusting the position of the proximal inner shaft relative to the proximal outer shaft, a distal portion of the proximal outer shaft disposed within a proximal portion of the distal inner shaft, the adjustment knob movable between a height position configured to allow for simultaneous actuation of the proximal and distal adjustment assemblies, a proximal position configured to allow for actuation of only the proximal adjustment assembly, and a distal position configured to allow for actuation of only the distal adjustment assembly.

19. The system according to claim 18, wherein the proximal adjustment assembly of the spinal implant includes a flange nut that is longitudinally movable to drive a change in the vertical height of the proximal region of the spinal implant, and the distal adjustment assembly of the spinal implant includes a threaded post that is longitudinally movable to drive a change in the vertical height of the distal region of the spinal implant, the flange nut including a threaded opening defined therethrough that is threadably engaged with the threaded post.

20. The system according to claim 19, wherein the outer shaft of the driving instrument includes an open distal tip having an inner surface configured to engage an outer surface of the flange nut, and the distal inner shaft of the driving instrument including a distal tip configured to engage a recessed proximal end of the threaded post.

21. A method of implanting a spinal implant into a disc space between adjacent vertebral bodies, the method comprising:
    inserting a spinal implant that is releasably attached to a distal end of an insertion instrument into a disc space, the spinal implant including:
        an upper body including an outer surface and an inner surface;
        a lower body including an outer surface and an inner surface, the inner surfaces of the upper and lower bodies disposed in opposed relation relative to each other;
        a proximal adjustment assembly disposed between the upper and lower bodies in the proximal region of the spinal implant and adjustably coupled to the upper and lower bodies; and
        a distal adjustment assembly disposed between the upper and lower bodies in the distal region of the spinal implant and adjustably coupled to the upper and lower bodies, wherein the proximal and distal adjustment assemblies are independently movable, both concurrently and alternately, to change a vertical height of at least one of the proximal region or the distal region of the spinal implant;
    inserting a driving instrument into a lumen defined through the insertion instrument and into engagement with the spinal implant, the driving instrument including:
        an outer shaft including a distal end configured to actuate the proximal adjustment assembly;
        a distal inner shaft disposed within the outer shaft and including a distal end configured to actuate the distal adjustment assembly; and
        a proximal shaft assembly including a proximal outer shaft, a proximal inner shaft disposed within the proximal outer shaft, and an adjustment knob for adjusting the position of the proximal inner shaft relative to the proximal outer shaft, a distal portion of the proximal outer shaft disposed within a proximal portion of the distal inner shaft, the adjustment knob movable between a height position configured to allow for simultaneous actuation of the proximal and distal adjustment assemblies, a proximal position configured to allow for actuation of only the proximal adjustment assembly, and a distal position configured to allow for actuation of only the distal adjustment assembly; and
    adjusting at least one of the proximal or distal adjustment assemblies of the spinal implant with the driving instrument.

22. The method according to claim 21, further comprising attaching the spinal implant to the distal end of the insertion instrument with the outer surfaces of the upper and lower bodies substantially parallel to each other.

23. The method according to claim 21, wherein adjusting at least one of the proximal or distal adjustment assemblies includes setting the driving instrument to the height position to actuate both the proximal and distal adjustment assemblies such that the upper and lower bodies of the spinal implant are expanded while maintaining the upper and lower bodies in substantially parallel relation to each other until the spinal implant engages the vertebral bodies.

24. The method according to claim 22, further comprising individually actuating at least one of the proximal or distal adjustment assemblies to adjust the height of at least one of the proximal or distal regions of the spinal implant to accommodate lordosis.

25. The method according to claim 21, wherein adjusting at least one of the proximal or distal adjustment assemblies includes setting the driving instrument to the proximal or distal position to individually actuate the proximal or distal adjustment assembly.

26. The method according to claim 21, further comprising locking the position of the spinal implant with a set screw.

27. The method according to claim 21, further comprising adjusting the vertical height of at least one of the proximal or distal regions of the spinal implant prior to inserting the spinal implant into the disc space.

* * * * *